US006492380B1

(12) United States Patent
Ross et al.

(10) Patent No.: US 6,492,380 B1
(45) Date of Patent: Dec. 10, 2002

(54) METHOD OF INHIBITING NEUROTROPHIN-RECEPTOR BINDING

(75) Inventors: Gregory M. Ross; Igor L. Shamovsky; Sandra Marone; Donald F. Weaver; Richard J. Riopelle, all of Kingston (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 09/457,606

(22) Filed: Dec. 8, 1999

Related U.S. Application Data

(63) Continuation of application No. 09/310,883, filed on May 17, 1999, now abandoned.

(51) Int. Cl.$^{7}$ .................... A61K 31/435; C07D 221/06
(52) U.S. Cl. .................... 514/290; 514/296; 546/101
(58) Field of Search .................... 546/79, 95, 98, 546/101; 514/290, 296

(56) References Cited

U.S. PATENT DOCUMENTS

| | | | |
|---|---|---|---|
| 3,821,383 A | 6/1974 | Sestanj | 423/258 |
| 4,204,063 A | 5/1980 | Braña | 546/99 |
| 4,254,109 A | 3/1981 | Sestanj | 424/178 |

(List continued on next page.)

FOREIGN PATENT DOCUMENTS

| | | | |
|---|---|---|---|
| DE | 2323555 A | 8/1974 | A61K/27/00 |
| DE | 3707652 A1 | 9/1988 | A61K/31/435 |
| EP | 0 268 093 A1 | 5/1988 | A61K/31/47 |
| EP | 0 206 322 A2 | 12/1996 | A61K/31/47 |
| FR | 2 521 139 A | 8/1983 | A61K/31/47 |
| WO | WO 98/17278 | 4/1998 | |
| WO | WO 98/34632 | 8/1998 | |
| WO | WO 98/52919 | 11/1998 | |
| WO | WO 00/00472 | 1/2000 | |

OTHER PUBLICATIONS

Laszlo Biczok et al , PCCP pp. 4759–4766, Aug. 23, 1999.*
Costi MP et al Naphthaimido derivatives as antifolate . . . , Eur. J. of Med Chem pp. 1011–1016, Jun. 24, 1996.*
Jaen, J.C. et al., "Kynurenic Acid Derivatives Inhibit the Binding of Nerve Growth Factor (NGF) to the Low–Affinity p75 NGF Receptor," *J. Med. Chem.* 38:4439–4445 (1995).
Spiegel, K. et al., "PD 90780, A Non Peptide Inhibitor of Nerve Growth Factor's Binding to the P75 NGF Receptor," *Biochemical and Biophysical Research Communications* 217(2):488–494 (Dec. 14, 1995).
Owolabi, J.B. et al., "Characterization of Antiallodynic Actions of ALE–0540, a Novel Nerve Growth Factor Receptor Antagonist, in the Rat," *J. of Pharmacology and Experimental Therapeutics* 289(3):1271–1276 (1999).

(List continued on next page.)

*Primary Examiner*—Alan L. Rotman
*Assistant Examiner*—Rita Desai
(74) *Attorney, Agent, or Firm*—Omar A. Nassif

(57) ABSTRACT

The present invention relates to compositions which inhibit the binding of nerve growth factor to the $p75^{NTR}$ common neurotrophin receptor and methods of use thereof. In one embodiment, the compound which inhibits binding of nerve growth factor to $p75^{NTR}$ comprises, particularly when bound to nerve growth factor, at least two of the following: (1) a first electronegative atom or functional group positioned to interact with $Lys^{34}$ of nerve growth factor; (2) a second electronegative atom or functional group positioned to interact with $Lys^{95}$ of nerve growth factor; (3) a third electronegative atom or functional group positioned to interact with $Lys^{88}$ of nerve growth factor; (4) a fourth electronegative atom or functional group positioned to interact with $Lys^{32}$ of nerve growth factor; and (5) a hydrophobic moiety which interacts with the hydrophobic region formed by $Ile^{31}$, $Phe^{101}$ and $Phe^{86}$ of nerve growth factor.

18 Claims, 5 Drawing Sheets

A-C denote electronegative atoms n = 3 - 5

U.S. PATENT DOCUMENTS

| | | | | |
|---|---|---|---|---|
| 4,874,863 | A | 10/1989 | Braña | 540/99 |
| 5,076,831 | A | 12/1991 | Saupe et al. | 71/90 |
| 5,183,821 | A | 2/1993 | Braña | 514/296 |
| 5,342,942 | A | 8/1994 | Jaen et al. | 544/250 |
| 5,420,137 | A | 5/1995 | Braña | 514/296 |
| 5,552,544 | A | 9/1996 | Braña | 544/126 |
| 5,554,622 | A | 9/1996 | Braña | 514/284 |
| 5,616,589 | A | 4/1997 | Keilhauer | 514/296 |

OTHER PUBLICATIONS

Bailleux, V. et al., "Synthesis and Anticonvulsant Activity of Some N–Phenylphthalimides," *Chem. Pharm. Bull.* 42(9):1817–1821 (1994).

Bailleux, V. et al., "Comparative Anticonvulsant Activity and Neurotoxicity of 4–Amino–N–(2,6–Dimethylphenyl)Phthalimide and Prototype Antiepileptic Drugs in Mice and Rats," *Epilepsia* 36(6):559–565 (1995).

Bailleux, V. et al., "Anticonvulsant activity of some 4–amino–N–phenylphthalimides and N–(3–amino–2–methylphenyl)phthalimides)," *Biomed & Pharmacother* 48:95–101 (1994).

Braña, M. F., et al. "Enediynes as Antitumor Compounds: Synthesis of Tetrahydropyridine Derivatives," *J. Org. Chem.,* 61: 1369–1374 (1996).

Braña, M. F., et al. "Synthesis and cytostatic activity of benz(de)iso–quinolin–1,3–diones. Structure–activity relationships," Eur. J. Med. Chem–Chimica Therapeutica, 16(3): 207–212 (1981 (May–Jun).

Arient, J. and Marhan, J., "Imidazolfarbstoffe VI. Synthese und Eigenschaften des 1,2–Naphtholylenbenzimidazols," *Collection Czechoslov. Chem. Commun.* 26: 2774–2780 (1961).

Nishizaki, S., "Infrared spectra of N–substituted naphthalimides," *Nippon Kaguku Zasshi* 86(7): 696–9 (1965) (Japan). (From Chem. Abstracts, 1966, 64 (3), Abstract No. 3321e.

Shibata, Y. et al. "Phenylphthalimides with Tumor Necrosis Factor Alpha Production–Enhancing Activity," *Chem. Pharm. Bull.* 44(1):156–162 (1996).

Chapman, J.M. Jr. et al., "Hypolipidemic Activity of Phthalimide Derivatives. 2. N–Phenylphthalimide and Derivatives," *J. Med. Chem.* 26:237–243 (1983).

Chapman, J.M. Jr. et al., "Hypolipidemic Activity of Phthalimide Derivatives. 3. A Comparison of Phthalimide and 1,2–Benzisothiazolin–3–one 1,1–Dioxide Derivatives to Phthalimidine and 1,2–Benzisothiazoline 1,1–Dioxide Congeners," *J. Med. Chem.* 26:243–246 (1983).

"Chapman, J.M. Jr. et al., Hypolipidemic Activity of Phthalimide Derivatives IV: Further Chemical Modification and Investigation of the Hypolipidemic Activity of N–Substitutes Imides," *J. Pharmaceutical Sciences* 72(11):1344–1347 (1983).

"Chapman, J.M. Jr. et al., Hypolipidemic Activity of Phthalimide Derivatives V: Reduced and Hydrolytic Products of Simple Cyclic Imides," *J. Pharmaceutical Sciences* 73(10):1482–1484 (1984).

Tyman J.H.P., "Fluorescent naphthalimide dyes", Chemical Abstract 108:7506 (1997).

Maybridge—Online Catalogue Search Page (2001–01–08).

Ryan Scientific Inc. Online Search Page (2001–01–08).

Donkor, et al., "Synthesis and biological activities of aldose reductase inhibitors bearing acyl benzensulfonamides as carboxylic acid surrogates", Eur. J. Med. Chem. 33: 15–22 (1998).

Donkor, et al., "Synthesis and biological activity of aldose reductase inhibitors with Michael acceptor substituents", Eur. J. Med. Chem. 34: 235–243 (1999).

Dubey, et al., "A novel bifunctional fluorescent tag for use in molecular biology", Indian J. Chem. 34B: 876–878 (Oct. 1995).

Hogdkiss, et al., "Fluorescent markers for hypoxic cells: a study of novel heterocyclic compounds that undergo bioreductive binding", Biochem. Pharmacol. 41:533–541 (1991).

Hodgkiss, et al., "Toxicity of 3–nitronaphthalimides to V79 379A Chinese hamster cells", Biochem. Pharmacol. 36: 1483–1487 (1987).

* cited by examiner

A-C denote electronegative atoms n = 3 - 5

Examples of the electronegative atoms (A, B and C)

Scheme1:

This synthetic scheme can be used to generate series of analogues possessing this general framework. The position of the substituent on the aromatic ring and the substituent itself can vary.

Scheme 2:

Scheme 3:

This synthetic scheme can be used to generate series of analogues possessing this general framework. The position of the substituent on the aromatic ring and the substituent itself can vary. $R_1$ is as previously defined.

METHOD OF INHIBITING NEUROTROPHIN-RECEPTOR BINDING

RELATED APPLICATION

This application is a continuation of U.S. Ser. No. 09/310,883, filed May 17, 1999, now abandoned the entire teachings of which are incorporated herein by reference.

BACKGROUND OF THE INVENTION

The neurotrophins are a family of structurally and functionally related proteins, including Nerve Growth Factor (NGF), Brain-Derived Neurotrophic Factor (BDNF), Neurotrophin-3 (NT-3), Neurotrophin-4/5 (NT-4/5) and Neurotrophin-6 (NT-6). These proteins promote the survival and differentiation of diverse neuronal populations in both the peripheral and central nervous systems (Hefti, 1986; Hefti and Weiner, 1986; Levi-Montalcini, 1987; Barde, 1989; Leibrock et al., 1989; Maisonpierre et al., 1990; Rosenthal et al., 1990; Hohn et al., 1990; Gotz et al., 1994; Maness et al., 1994) and are involved in the pathogenesis of diverse neurological disorders. Neurotrophins exert many of their biological effects through specific interactions with a class of transmembrane receptor tyrosine kinases (trkA, trkB and trkC) (Kaplan et al., 1991; Klein et al., 1991, 1992; Soppet et al., 1991; Squinto et al., 1991; Berkemeier et al., 1991; Escandon et al., 1993; Lamballe et al., 1991). Specificity of neurotrophin action results from their selective interactions with the trk receptors. That is, trkA only binds NGF (Kaplan et al., 1991; Klein et al., 1991); trkB binds BDNF and NT-4/5 (Soppet et al., 1991; Squinto et al., 1991; Berkemeier et al., 1991; Escandon et al., 1993; Lamballe et al., 1991; Klein et al., 1992; Vale and Shooter, 1985; Barbacid, 1993); and trkC exclusively binds NT-3 (Lamballe et al., 1991; Vale and Shooter, 1985). This is particularly evident when the trk receptors are coexpressed with the common neurotrophin receptor $p75^{NTR}$. (For review see Meakin and Shooter, 1992; Barbacid, 1993; Chao, 1994; Bradshaw et al., 1994; Ibáñez, 1995).

The common neurotrophin receptor $p75^{NTR}$ is a transmembrane glycoprotein structurally related to the tumor necrosis factor and CD-40 receptors (Meakin and Shooter, 1992; Rydén and Ibáñez, 1996). As all neurotrophins bind to $p75^{NTR}$ with similar affinity (Rodriguez-Tébar et al., 1990; Hallböök et al., 1991; Rodriguez-Tébar et al., 1992; Ibáñez, 1995), neurotrophin specificity is conventionally thought to be caused by the binding selectivity for trk receptors which are differentially expressed in different neuronal populations (Ibáñez, 1995). However, accumulated experimental data on neurotrophin activity reveal important functional aspects of $p75^{NTR}$ (Heldin et al., 1989; Jing et al., 1992; Herrmann, 1993; Barker and Shooter, 1994; Dobrowsky et al., 1994, Matsumoto et al., 1995; Marchetti et al., 1996; Washiyama et al., 1996). The common neurotrophin receptor enhances functions and increases binding specificity of trk receptors (Barker and Shooter, 1994; Mahadeo et al., 1994; Chao and Hempstead, 1995; Rydén and Ibáñez, 1996). In addition, $p75^{NTR}$ possesses unique, trk-independent signaling properties which involve ceramide production through activation of the sphingomyelin cycle (Dobrowsky et al., 1994), apoptosis (cell death) (Van der Zee et al., 1996; Cassacia-Bonnefil et al., 1996; Frade et al., 1996), and activation of the transcription factor NFκB (Carter et al., 1996). Recently, $p75^{NTR}$ has been demonstrated to participate in human melanoma progression (Herrmann et al., 1993; Marchetti et al., 1996). Furthermore, NGF and NT-3 increase the production of heparin by 70W melanoma cells, which is associated with their metastatic potential (Marchetti et al., 1996). Although this effect has been shown to be mediated by the common neurotrophin receptor, neither BDNF nor NT-4/5 appeared to be active.

Due to the implication of NGF/$p75^{NTR}$ binding in various disease states, a need exists for pharmaceutical agents and methods of use thereof for interfering with the binding of NGF to the $p75^{NTR}$ common neurotrophin receptor.

SUMMARY OF THE INVENTION

The present invention relates to the discovery of molecular structural features which contribute to the ability of a compound to inhibit the binding of NGF to the common neurotrophin receptor $p75^{NTR}$. Compounds which have these features are of use, for example, for inhibiting binding of NGF to $p75^{NTR}$. Such compounds can also be used to treat a patient having a condition which is mediated, at least in part, by the binding of NGF to $p75^{NTR}$.

In one embodiment, the present invention relates to compositions which inhibit the binding of nerve growth factor to the $p75^{NTR}$ common neurotrophin receptor and methods of use thereof.

In one embodiment, the compound which inhibits binding of nerve growth factor to $p75^{NTR}$ comprises at least two of the following: (1) a first electronegative atom or functional group positioned to interact with $Lys^{34}$ of nerve growth factor; (2) a second electronegative atom or functional group positioned to interact with $Lys^{95}$ of nerve growth factor; (3) a third electronegative atom or functional group positioned to interact with $LyS^{88}$ of nerve growth factor; (4) a fourth electronegative atom or functional group positioned to interact with $Lys^{32}$ of nerve growth factor; and (5) a hydrophobic moiety which interacts with the hydrophobic region formed by amino acid residues of nerve growth factor, including $Ile^{31}$, $Phe^{101}$ and $Phe^{86}$. Such inhibitors, preferably, bind nerve growth factor via at least two of the foregoing interactions.

In one embodiment, compounds which inhibit binding of nerve growth factor to $p75^{NTR}$ have Formula 1, (1)

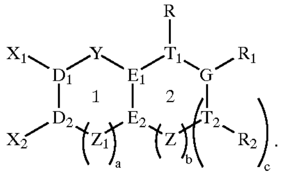

In Formula 1, $D_1$, $D_2$, $E_1$, $E_2$ and G are each, independently, an $sp^2$-hybridized carbon or nitrogen atom. One of $X_1$ and $X_2$ is a hydrogen atom or absent, while the other is an electronegative atom or an electronegative functional group. R and $R_2$ are each, independently, an electronegative atom or an electronegative functional group, such as O, S, $CH_2$, or $NR_3$, where $R_3$ is H, alkyl, preferably $C_1$–$C_6$-alkyl, or aryl, such as phenyl. R, $R_2$ and one of $X_1$ and $X_2$ can also each be, independently, an electronegative atom or functional group, such as alkylcarbonyl; alkylthiocarbonyl; alkoxycarbonyl; aminocarbonyl; —OH; —CN; —$CO_2H$; —$SO_3H$; —$SO_2H$; —$PO_3H_2$; —$NO_2$; —$ONO_2$, —CNO, —SH, —CNS, —$OSO_3H$, —OC(O)(OH); halomethyl, dihalomethyl or trihalomethyl group or a fluorine, chlorine, bromine or iodine atom. Y is N, O, S, C—L or N—L, where L is H, alkyl, preferably $C_1$–$C_6$-alkyl, or an electronegative atom or functional group, such as, but not limited to, alkylcarbonyl;

alkylthiocarbonyl; alkoxycarbonyl; aminocarbonyl; —OH; —CN; —$CO_2H$; —$SO_3H$; —$SO_2H$; —$PO_3H_2$; —$NO_2$; —$ONO_2$,—CNO, —SH, —CNS, —$OSO_3H$, —OC(O)(OH); halomethyl, dihalomethyl or trihalomethyl groups or a halogen atom, such as a fluorine, chlorine, bromine or iodine atom. Z and $Z_1$ are each, independently, O, S, CH, C(O), N, NH, N-alkyl, N-cycloalkyl and N—P, where P is a carbohydrate moiety, such as a monosaccharide group, for example, a fucosyl, glucosyl, galactosyl, mannosyl, fructosyl, gulosyl, idosyl, talosyl, allosyl, altrosyl, ribosyl, arabinosyl, xylosyl or lyxosyl group. $T_1$ and $T_2$ are each, independently, an $sp^2$- or $sp^3$-hybridized carbon or nitrogen atom. a, b, and c are each 0 or 1, provided that at least one of b and c is 1. $R_1$ is a monocyclic or polycyclic aryl or heteroaryl, monosaccharide or oligosaccharide, alkyl, cycloalkyl, arylalkyl, alkylamino or alkoxy group which is substituted with at least one substituent selected from the group consisting of electronegative atoms and electronegative functional groups.

It will be appreciated that in this and the following structures, the lines connecting the variables can be single or double bonds. In addition, hydrogen atoms are added to the variables as necessary to complete the valence of the atom.

In another embodiment, compounds have Formula 3, In another embodiment, the NGF/$p75^{NTR}$ binding inhibitor has Formula 3

(3)

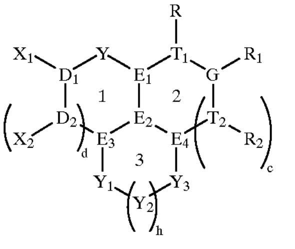

where $D_1$, $D_2$, $X_1$, $X_2$, Y, $E_1$, $E_2$, $T_1$, $T_2$, R, G, $R_1$, $R_2$, and c have the meanings given above for these variables in Formula 1. $Y_1$, $Y_2$, and $Y_3$ are independently selected from the identities given for Y in Formula 1. $E_3$ and $E_4$ are each, independently, an $sp^2$-hybridized carbon or nitrogen atom, and d and h are, independently, 0 or 1.

In another embodiment, compounds which inhibit the binding of nerve growth factor to $p75^{NTR}$ have Formula 2, (2)

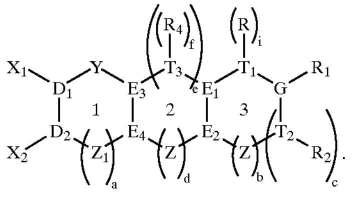

In Formula 2, $D_1$, $D_2$, $E_1$, $E_2$, $E_3$, $E_4$ and G are each, independently, an $sp^2$-hybridized carbon or nitrogen atom. One of $X_1$ and $X_2$ is a hydrogen atom or absent, while the other is an electronegative atom or an electronegative functional group. R, $R_2$ and $R_4$ are each, independently, an electronegative atom or electronegative functional group, such as O, S, $CH_2$, or $NR_3$, where $R_3$ is H, OH, alkyl, preferably $C_1$–$C_6$-alkyl, or aryl, such as phenyl. R, $R_2$ and one of $X_1$ and $X_2$ can also each be, independently, an electronegative atom or functional group, such as alkylcarbonyl; alkylthiocarbonyl; alkoxycarbonyl; aminocarbonyl; —OH; —CN; —$CO_2H$; —$SO_3H$; —$SO_2H$; —$PO_3H_2$; —$NO_2$; —$ONO_2$, —CNO, —SH, —CNS, —$OSO_3H$, —OC(O)(OH); halomethyl, dihalomethyl or trihalomethyl group or a fluorine, chlorine, bromine or iodine atom. Y is N, O, S, C—L or N—L, where L is H, alkyl, preferably $C_1$–$C_6$-alkyl, or an electronegative atom or functional group, such as, but not limited to, alkylcarbonyl; alkylthiocarbonyl; alkoxycarbonyl; aminocarbonyl; —OH; —CN; —$CO_2H$; —$SO_3H$; —$SO_2H$; —$PO_3H_2$; —$NO_2$; —$ONO_2$, —CNO, —SH, —CNS, —$OSO_3H$, —OC(O)(OH); halomethyl, dihalomethyl or trihalomethyl groups or a halogen atom, such as a fluorine, chlorine, bromine or iodine atom. Z and $Z_1$ are each, independently, O, S, CH, C(O), N, NH, N-alkyl, N-cycloalkyl and N—P, where P is a carbohydrate moiety, such as a monosaccharide group, for example, a fucosyl, glucosyl, galactosyl, mannosyl, fructosyl, gulosyl, idosyl, talosyl, allosyl, altrosyl, ribosyl, arabinosyl, xylosyl or lyxosyl group. $T_1$, $T_2$ and $T_3$ are each, independently, an $sp^2$- or $sp^3$-hybridized carbon or nitrogen atom. When f is 0, $T_3$ can further have the meanings given for Z and $Z_1$ above. a, b, c, d, e, f, g, h and i are each 0 or 1, provided that at least one of b and c is 1, at least one of d and e is 1 and at least one of f and i is 1. $R_1$ is a monocyclic or polycyclic aryl or heteroaryl, monosaccharide or oligosaccharide, alkyl, cycloalkyl, arylalkyl, alkylamine or alkoxy group which is substituted with at least one substituent selected from the group consisting of electronegative atoms and electronegative functional groups.

In another embodiment, a compound which inhibits the binding of NGF to $p75^{NTR}$ has Formula 5, (5)

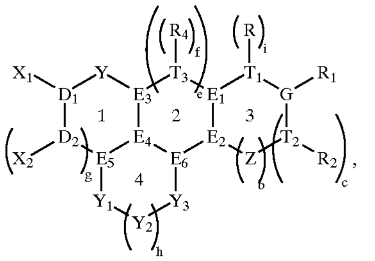

wherein $D_1$, $D_2$, $X_1$, $X_2$, $E_1$, $E_2$, $E_3$, $T_1$, $T_2$, $T_3$, Z, G, R, $R_1$, $R_2$, $R_4$, b, e, f, i, and c have the meanings given for these variables in Formula 2. $Y_1$, $Y_2$, and $Y_3$ are independently selected from the identities given for Y in Formula 2, and h is 0 or 1. $E_5$ and $E_6$ are each, independently, an sp2-hybridized carbon or nitrogen atom, and g is 0 or 1. Ring 4 can be further unsubstituted or substituted with one or more substituents, such as alkyl or aryl groups.

In another embodiment, the invention provides a pharmaceutical composition comprising at least one compound of the invention, or pharmaceutically acceptable salt thereof, in combination with a pharmaceutically acceptable carrier or excipient.

The invention also provides a method of inhibiting the binding of nerve growth factor to the $p75^{NTR}$ receptor. The method comprises contacting cells which express the $p75^{NTR}$ receptor with a nerve growth factor/$p75^{NTR}$ binding inhibitor of the invention in an amount which is sufficient to inhibit binding of nerve growth factor to the $p75^{NTR}$ receptor. The method can be practiced in vivo or in vitro.

In another embodiment, the invention relates to a method of treating a condition in a patient which is mediated by the binding of nerve growth factor to the $p75^{NTR}$ receptor. The method comprises administering to the patient a therapeutically effective amount of a nerve growth factor/p75$^{NTR}$ binding inhibitor of the invention. Preferably, the compound to be administered selectively inhibits the binding of nerve growth factor to p75$^{NTR}$ in cells which do not express the NGF receptor trkA.

DETAILED DESCRIPTION OF THE INVENTION

Figure 1:
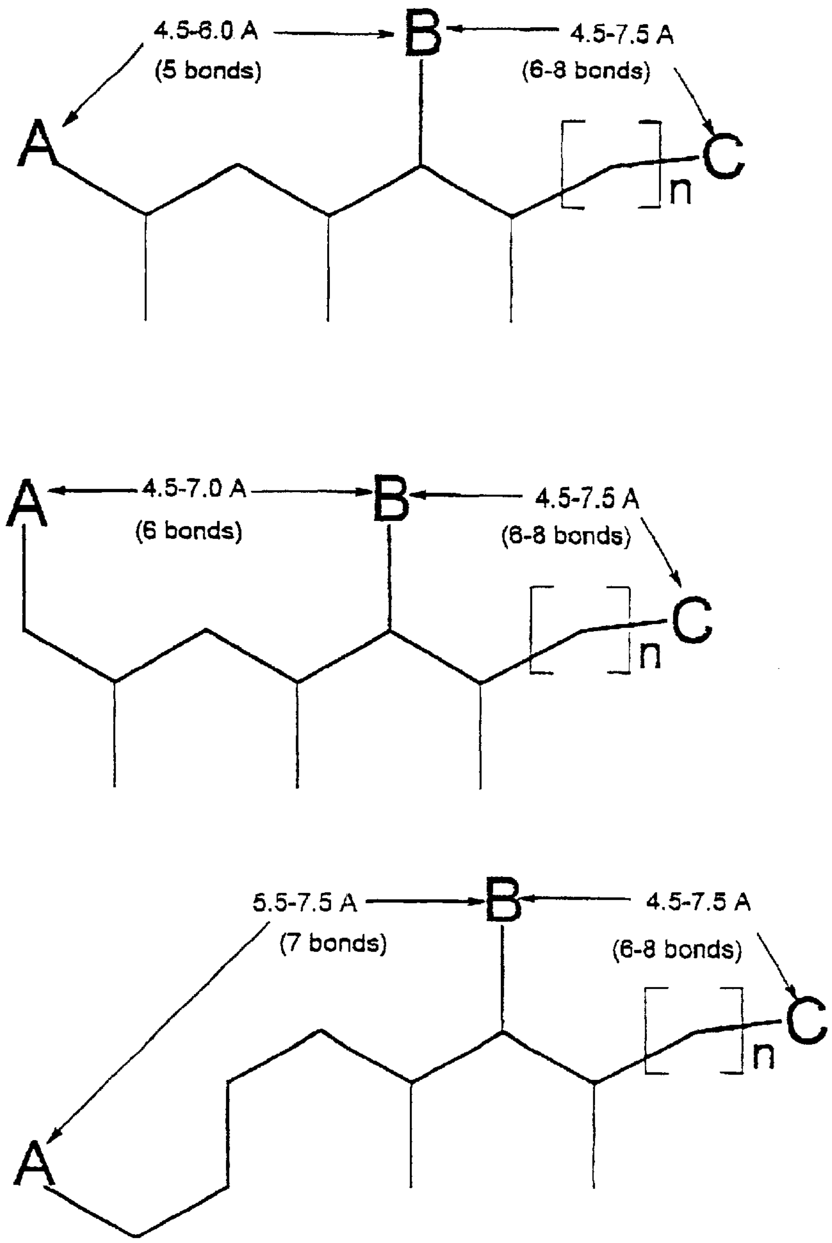
FIG. 1 illustrates examples of suitable configurations for electronegative atoms in the NGF/p75$^{NTR}$ binding inhibitors of the invention.

Nerve growth factor (also referred to hereinafter as "NGF") is a neurotrophin implicated in the pathogenesis of Alzheimer's disease, epilepsy and pain (Ben and Represa, 1990; McKee et al., 1991; Leven and Mendel, 1993; Woolf and Doubell, 1994; Rashid et al., 1995; McMahon et al., 1995). The binding of NGF to its receptors is determined by distinct sequences within its primary amino acid structure. While several regions of NGF participate in the NGF/trkA interaction, mutation studies suggest that relatively few key residues, namely those located in the NGF amino and carboxyl termini, are required for high affinity binding.

NGF displays high and low affinity binding sites in sensory and sympathetic neurons and in pheochromocytoma PC12 cells (Sutter et al., 1979; Landreth and Shooter, 1980; Schechter and Bothwell, 1981). The coexpression of the common neurotrophin p75$^{NTR}$ receptor with trkA is required to form the high affinity binding site (Hempstead et al., 1991; Barker and Shooter, 1994; Mahadeo et al., 1994; Chao and Hempstead, 1995). Several models of the trkA-p75$^{NTR}$ interaction have been proposed to explain high affinity NGF binding (Bothwell, 1991; Chao, 1992b; Chao and Hempstead, 1995; Wolf et al., 1995; Ross et al., 1996; Ross et al., 1997). These models differ with respect to direct (conformational model) or indirect (ligand-presentation model) interaction of p75$^{NTR}$ with trkA. Direct trkA-p75$^{NTR}$ interaction is consistent with much of the existing experimental data.

The hairpin loop at residues 29–35 of NGF is responsible for recognition by p75$^{NTR}$ (Ibáñez et al., 1992; Radziejewski et al., 1992), while the amino and carboxyl termini are important binding determinants for recognition by the trkA receptor (Shih et al., 1994; Moore and Shooter, 1975; Suter et al., 1992; Burton et al., 1992; Kahle et al., 1992; Luo and Neet, 1992; Drinkwater et al., 1993; Treanor et al., 1995; Taylor et al., 1991; Shamovsky et al., 1998; Shamovsky et al., 1999; WO 98/06048). Truncation of either the amino or carboxyl terminus of NGF produces less active NGF analogues; similarly most deletion or point mutations of the amino terminus also lead to NGF analogues with diminished activity (Shih et al., 1994; Burton et al., 1992, 1995; Kahle et al., 1992; Drinkwater et al., 1993; Treanor et al., 1995; Taylor et al., 1991). On the other hand, the NGFΔ2–8 (NGF with residues 2–8 removed) and NGFΔ3–9 deletion mutants are almost as active as wild type NGF (Drinkwater et al, 1993). These NGF structure-activity relationships in combination with the considerable species variability (mouse, human, guinea pig and snake) of the amino acid sequence of the NGF termini (McDonald et al., 1991) are of potential value in understanding the NGF/trkA interaction.

NGF exerts its biological activity as a non-covalent dimer (Treanor et al., 1995; Burton et al., 1995; McDonald et al., 1991; Ibáñez et al., 1993; Bothwell and Shooter, 1977). Two 118 residue NGF monomers are dimerized by hydrophobic and van der Waals interactions between their three antiparallel pairs of β-strands; consequently, the amino terminus of one NGF monomer and the carboxyl terminus of the other are spatially juxtaposed (McDonald et al, 1991). Furthermore, although a dimer has 2 pairs of termini, only one pair of termini is required for trkA receptor recognition (Treanor et al., 1995; Burton et al, 1995).

The X-ray crystallographic 3-dimensional structure of a dimeric mouse NGF (mNGF) has been reported (McDonald et al., 1991). However, within this structure, the amino terminus (residues 1–11) and the carboxyl terminus (residues 112–118) remain unresolved for both pairs of termini. High flexibility of the NGF termini makes it difficult to experimentally determine their bioactive conformations, particularly since transition metal ions commonly used in X-ray crystallography (McDonald et al., 1991) have high affinity for His residues (Gregory et al., 1993) which are present in the NGF amino terminus (Bradshaw et al., 1994). Indeed, conformational alterations in the receptor binding domains of NGF caused by $Zn^{2+}$ cations leading to its inactivation have been described recently (Ross et al., 1997). Since the amino and carboxyl termini are crucial for NGF bioactivity as mediated via trkA and because of the significance of NGF in multiple neurologic disease processes, the determination of the biologically active coloration of these termini is an important and challenging problem for computational chemistry.

The present invention relates to the discovery of molecular structural features which contribute to the ability of a compound to inhibit the binding of NGF to the common neurotrophin receptor p75$^{NTR}$ Compounds which have these features are of use, for example, for inhibiting binding of NGF to p75$^{NTR}$ Such compounds can also be used to treat a patient having a condition which is mediated, at least in part, by the binding of NGF to p75$^{NTR}$.

Certain compounds which inhibit the binding of NGF to p75$^{NTR}$ are disclosed in copending U.S. patent application Ser. No. 09/292,450, incorporated herein by reference in its entirety.

In one embodiment, the present invention provides compounds which inhibit the binding of nerve growth factor (NGF) to the p75$^{NTR}$ receptor. The compounds have at least two of the following characteristics: (1) a first electronegative atom or functional group positioned to interact with $Lys^{34}$ of NGF; (2) a second electronegative atom or functional group positioned to interact with $Lys^{95}$ of NGF; (3) a third electronegative atom positioned to interact with $Lys^{88}$ of NGF; (4) a fourth electronegative atom or functional group positioned to interact with $Lys^{32}$ of NGF; and (5) a hydrophobic moiety which interacts with the hydrophobic region formed by $Ile^{31}$, $Phe^{101}$ and $Phe^{86}$ of NGF. A compound having two or more of these structural attributes is referred to herein as an "NGF/p75$^{NTR}$ binding inhibitor". Preferably, the NGF/p75$^{NTR}$ binding inhibitor has at least three of the foregoing attributes when bound to NGF, more preferably at least four such attributes. Most preferably, the NGF/p75$^{NTR}$ binding inhibitor has each of the five foregoing attributes. Typically, an NGF/p75$^{NTR}$ binding inhibitor of the invention interacts with NGF via at least two of the foregoing interactions when bound to NGF.

The term "electronegative atom", as used herein, refers to an atom which carries a partial or full negative charge in a particular compound under physiological conditions. The electronegative atom can be, for example, an oxygen atom, a nitrogen atom, a sulfur atom or a halogen atom, such as a fluorine, chlorine, bromine or iodine atom. Preferably the electronegative atom is an oxygen atom. The term "electronegative functional group", as used herein, refers to a functional group which includes at least one electronegative atom. Electronegative groups include acid functional groups and other polar functional groups. For example, suitable electronegative functional groups include, but are not limited to, carbonyl, thiocarbonyl, ester, imino, amido, carboxylic acid, sulfonic acid, sulfinic acid, sulfamic acid, phosphonic acid, boronic acid, sulfate ester, hydroxyl, mercapto, cyano, cyanate, thiocyanate, isocyanate, isothiocyanate, carbonate, nitrate and nitro groups. It is to be understood that, unless otherwise indicated, reference herein to an acidic functional group also encompasses salts of that functional group in combination with a suitable cation.

An electronegative atom of the NGF/p75$^{NTR}$ binding inhibitor bears a full or partial negative charge under physiological conditions and can, therefore, interact electrostatically with the positively charged side chain of an NGF lysine residue. This will be an interaction, such as, for example, a hydrogen bond, an ion/ion interaction, an ion/dipole interaction or a dipole/dipole interaction. The hydrophobic region or moiety of the NGF/p75$^{NTR}$ binding inhibitor can interact with a hydrophobic region of NGF via a hydrophobic interaction. Without being bound by theory, it is believed that compounds having the disclosed structural features can interact with NGF in such a way as to interfere with, and thereby inhibit, the binding of NGF to p75$^{NTR}$.

Figure 2:
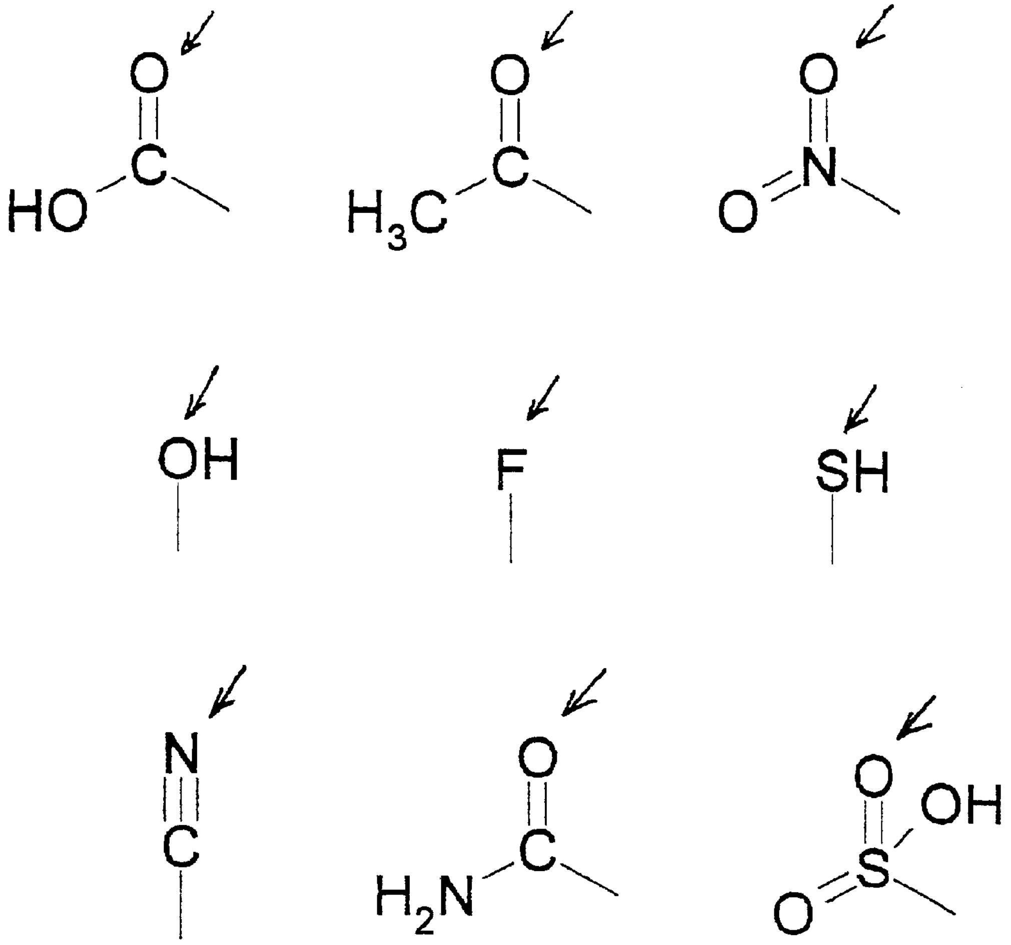
FIG. 2 illustrates examples of electronegative functional groups.

The ability of a compound to interact with the amino acid residues of NGF specified above can be determined using a structural model of NGF obtained using a energy-minimization algorithm, as described in published PCT application WO 98/06048, incorporated herein by reference in its entirety. For example, a molecule will interact with the specified residues of NGF, as discussed above, if it has at least 3 electronegative atoms (A, B and C) such that at least one of the following two conditions is satisfied: (i) atoms A and B are separated by 5–7 covalent bonds, B and C are separated by 6–8 covalent bonds, and A and C are separated by 10–14 covalent bonds and (ii) distance between A and B is between 4.5 and 7.5 angstroms, and distance between B and C is between 4.5 and 7.5 angstroms. The number of covalent bonds separating atoms can be determined from the structural formula of a molecule. Distance between atoms can be determined experimentally (e.g., by X-ray crystallography or NMR spectroscopy) or evaluated theoretically using any molecular builder (e.g., SYBYL from Tripos Inc. (St. Louis, Mo., USA) or QUANTA from Molecular Simulations Inc.(San Diego, Calif., USA) as well as any molecular modeling technique (e.g., AMBER from Oxford Molecular Group Inc. /University of California, San Francisco or CHARMm from Molecular Simulations Inc.) or quantum chemical technique (e.g., MNDO from Oxford Molecular Group Inc. (Campbell, Calif. USA) /University of Zurich; AMPAC from Semichem (Kansas City, Mo., USA); CADPAC from Oxford Molecular Group Inc./Cambridge University; Gaussian-98 from Gaussian Inc. (Carnegie, Pa., USA); or GAMESS from Iowa State University). Examples of suitable configurations of groups A, B and C are illustrated in FIG. 1, while a representative group of electronegative functional groups is shown in FIG. 2.

Preferred NGF/p75$^{NTR}$ inhibitors of the invention comprise a molecular scaffold or framework, to which the electronegative atoms or functional groups are attached, either directly or via an intervening moiety. The scaffold can be, for example, a cyclic or polycyclic moiety, such as a monocyclic, bicyclic or tricyclic moiety, and can include one or more hydrocarbyl or heterocyclic rings. Preferably, the scaffold includes two or more fused, planar, five- or six-membered rings. The molecular scaffold presents the attached electronegative atoms, electronegative functional groups or a combination thereof, in the proper configuration or orientation for interaction with the appropriate residues of NGF. In addition, the molecular scaffold, such as polycyclic system, or a portion thereof, can serve as the hydrophobic group which interacts with hydrophobic residues of NGF, as described above.

In one embodiment, the NGF/p75$^{NTR}$ inhibitor is of general Formula 1, (1)

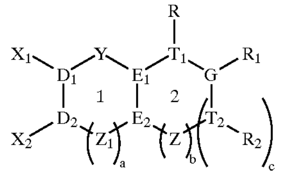

In Formula 1, $D_1$, $D_2$, $E_1$, $E_2$ and G are each, independently, an $sp^2$-hybridized carbon or nitrogen atom. One of $X_1$ and $X_2$ is a hydrogen atom or absent, while the other is an electronegative atom or an electronegative functional group. R and $R_2$ are each, independently, an electronegative atom or an electronegative functional group, such as O, S, $CH_2$, or $NR_3$, where $R_3$ is H, alkyl, preferably $C_1$–$C_6$-alkyl, or aryl, such as phenyl. R, $R_2$ and one of $X_1$ and $X_2$ can also each be, independently, an electronegative atom or functional group, such as alkylcarbonyl; alkylthiocarbonyl; alkoxycarbonyl; aminocarbonyl; —OH; —CN; —$CO_2H$; —$SO_3H$; —$SO_2H$; —$PO_3H_2$; —$NO_2$; —$ONO_2$, —CNO, —SH, —CNS, —$OSO_3H$, —OC(O)(OH); halomethyl, dihalomethyl or trihalomethyl group or a fluorine, chlorine, bromine or iodine atom. Y is N, O, S, C—L or N—L, where L is H, alkyl, preferably $C_1$–$C_6$-alkyl, or an electronegative atom or functional group, such as, but not limited to, alkylcarbonyl; alkylthiocarbonyl; alkoxycarbonyl; aminocarbonyl; —OH; —CN; —$CO_2H$; —$SO_3H$; —$SO_2H$; —$PO_3H_2$; —$NO_2$; —$ONO_2$, —CNO, —SH, —CNS, —$OSO_3H$, —OC(O)(OH); halomethyl, dihalomethyl or trihalomethyl groups or a halogen atom, such as a fluorine, chlorine, bromine or iodine atom. Z and $Z_1$ are each, independently, O, S, CH, C(O), N, NH, N-alkyl, N-cycloalkyl and N—P, where P is a carbohydrate moiety, such as a monosaccharide group, for example, a fucosyl, glucosyl, galactosyl, mannosyl, fructosyl, gulosyl, idosyl, talosyl, allosyl, altrosyl, ribosyl, arabinosyl, xylosyl or lyxosyl group. $T_1$ and $T_2$ are each, independently, an $sp^2$- or $sp^3$-hybridized carbon or nitrogen atom. a, b and c are each 0 or 1, provided that at least one of b and c is 1.

$R_1$ is a monocyclic or polycyclic aryl or heteroaryl, mono- or oligosaccharide, alkyl, cycloalkyl, arylalkyl, alkylamino or alkoxy group which is substituted with at least one substituent selected from the group consisting of electronegative atoms and electronegative functional groups. Preferred monosaccharide groups include fucosyl, glucosyl, galactosyl, mannosyl, fructosyl, gulosyl, idosyl, talosyl, allosyl, altrosyl, ribosyl, arabinosyl, xylosyl and lyxosyl groups. The electronegative substituent can be bonded to the aryl or heteroaryl ring system, alkyl, cycloalkyl, or oligo- or monosaccharide group either directly or indirectly via a bridging group, for example, an alkylene group such as a $C_1$–$C_4$-alkylene group or an oxaalkylene group. Suitable directly bonded and alkylene bridged electronegative atoms and functional groups include, but are not limited to, alkylcarbonyl; alkylthiocarbonyl; alkoxycarbonyl; aminocarbonyl; —OH; —CN; —$CO_2H$; —$SO_3H$; —$SO_2H$; —$PO_3H_2$; —$NO_2$; —$ONO_2$, —CNO, —SH, —CNS, —$OSO_3H$; —OC(O)(OH); carboxyalkyl, nitroalkyl, N,N-dialkylaminosulfonyl, aminocarbonyl, alkoxycarbonyl, alkoxycarbonylalkyl, cyanocarbonylalkyl, haloalkyl, such as fluoromethyl, difluoromethyl, trifluoromethyl, chloromethyl, dichloromethyl or trichloromethyl; alkyamido or a halogen atom, such as a fluorine, chlorine, bromine or iodine atom. In one embodiment, $R_1$ is selected from the group consisting of groups including, but not limited to, —$(CH_2)_aCOOH$; —$(CH_2)_aNO_2$; —$(CH_2)_aOH$; —$(CH_2)_aPO_3H_2$; —$(CH_2)_aSO_3H$; —$(CH_2)_aSO_2H$; —$R_4(CH_2)_aCOOH$; —$R_4(CH_2)_aNO_2$; —$R_4(CH_2)_aPO_3H_2$; —$R_4(CH_2)_aSO_2H$; —$R_4(CH_2)_aSO_3H$; and —$R_4(CH_2)_aOH$, where a is 1 to 12, preferably 1 to about 4, and $R_4$ is NH or O.

Rings 1 and 2 are each, independently, a five- or six-membered ring and, preferably, are both planar.

It is to be understood that compounds of Formula 1 and Formulas 2, 3 and 5, below, will further include double bonds between adjacent atoms as required to satisfy the valence of each atom. That is, double bonds are added to provide the following number of total bonds to each of the following types of atoms: carbon: four bonds; nitrogen: 3 bonds; oxygen: two bonds; and sulfur: two bonds.

The term "alkyl", as used herein, refers to a normal, branched or cyclic aliphatic hydrocarbyl group, which can be saturated or partially unsaturated. Preferred alkyl groups are normal, branched and cyclic $C_1$–$C_8$-alkyl and -alkenyl groups.

In another embodiment, the NGF/p75$^{NTR}$ binding inhibitor of Formula 3

(3)

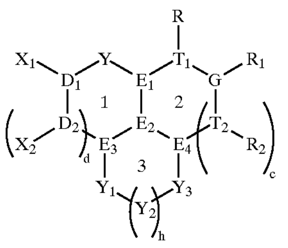

where $D_1$, $D_2$, $X_1$, $X_2$, Y, $E_1$, $E_2$, $T_1$, $T_2$, R, G, $R_1$, $R_2$, and c have the meanings given above for these variables in Formula 1. $Y_1$, $Y_2$, and $Y_3$ are independently selected from the identities given for Y in Formula 1. $E_3$ and $E_4$ are each, independently, an $sp^2$-hybridized carbon or nitrogen atom, and d and h are each, independently, 0 or 1.

In one embodiment of the compounds of Formula 3, $R_1$ is a mono- or polycyclic aryl or heteroaryl, oligo- or monosaccharide group which is substituted with at least one electronegative atom or electronegative group. The mono- or polycyclic aryl or heteroaryl group is preferably substituted with an acid functional group, such as —$CO_2H$; —$SO_3H$; —$SO_2H$; —$PO_3H_2$; —$OSO_3H$; HOC(O)-alkyl; $HOS(O)_2$-alkyl; HOS(O)-alkyl; $(OH)_2P(O)$-alkyl; and $HOS(O)_2O$-alkyl; where the alkyl group is preferably a $C_1$–$C_4$-alkyl group. In another embodiment, the electronegative atom or electronegative functional group is selected from the group consisting of alkylcarbonyl; alkylthiocarbonyl; alkoxycarbonyl; —CN; —$NO_2$; —$ONO_2$, —CNO, —SH, —CNS, nitroalkyl, N,N-dialkylaminosulfonyl, aminocarbonyl, alkoxycarbonyl, alkoxycarbonylalkyl, cyanocarbonylalkyl, fluoromethyl, difluoromethyl, trifluoromethyl, chloromethyl, dichloromethyl, trichloromethyl, acetamido and halogen atoms. $R_1$ can also be an alkylamino, alkyl or alkoxy group which is substituted with at least one electronegative atom or functional group. For example, in one embodiment, $R_1$ is selected from the group consisting of —$(CH_2)_aNO_2$; —$(CH_2)_aOH$; —$(CH_2)_aPO_3H_2$; —$(CH_2)_aSO_3H$; —$(CH_2)_aSO_2H$; —$O(CH_2)_aCOOH$; —$O(CH_2)_aNO_2$; —$O(CH_2)_aPO_3H_2$; —$O(CH_2)_aSO_2H$; —$O(CH_2)_aSO_3H$; —$O(CH_2)_aOH$; —$NH(CH_2)_aCOOH$; —$NH(CH_2)_aNO_2$; —$NH(CH_2)_aPO_3H_2$; —$NH(CH_2)_aSO_2H$—; and $NH(CH_2)_aSO_3H$; where a is 1 to 12, preferably 1 to about 4.

In another embodiment of the compounds of Formula 3, $R_1$ is a phenyl group which is substituted by p-toluenesulfonamido or hydroxyl; or $R_1$ is a —$NH(CH_2)_aOH$ group, where a is 1 to about 4; a carboxyalkyl group, for example, a linear or branched carboxy-$C_1$–$C_8$-alkyl group; an alkoxycarbonyl group, such as a linear or branched $C_1$–$C_8$-alkoxycarbonyl group or an alkylcarbonate group, such as a linear or branched $C_1$–$C_8$-alkylcarbonate group. In this embodiment, ring atom is an $sp^2$-hybridized carbon atom, except for G, which is a nitrogen atom; R and $R_2$ are both O; and d, c and h are each 1.

Preferred compounds of Formula 3 are of the formula (4)

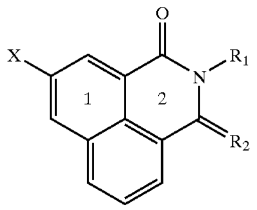

where X and $R_1$ have the meanings given above for these variables in Formula 1, $R_2$ is O, $CH_2$ or $NR_3$, where $R_3$ is H, alkyl, preferably $C_1$–$C_6$-alkyl, or aryl, and rings 1 and 4 can, optionally, independently be further substituted. Suitable substituents include alkyl groups, preferably normal or branched $C_1$–$C_6$-alkyl groups.

In another embodiment, the NGF/p75$^{NTR}$ binding inhibitor is of Formula 2, (2)

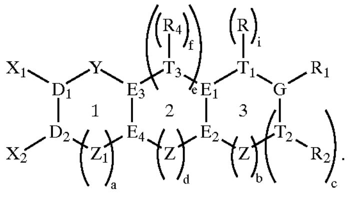

In Formula 2, $D_1$, $D_2$, $E_1$, $E_2$, $E_3$, $E_4$ and G are each, independently, an $sp^2$-hybridized carbon or nitrogen atom. One of $X_1$ and $X_2$ is a hydrogen atom or absent, while the other is an electronegative atom or an electronegative functional group. R, $R_2$ and $R_4$ are each, independently, an electronegative atom or an electronegative functional group, such as O, S, $CH_2$, or $NR_3$, where $R_3$ is H, alkyl, preferably $C_1$–$C_6$-alkyl, or aryl, such as phenyl. R, $R_2$ and one of $X_1$ and $X_2$ can also each be, independently, an electronegative atom or functional group, such as alkylcarbonyl; alkylthiocarbonyl; alkoxycarbonyl; aminocarbonyl; —OH; —CN; —$CO_2H$; —$SO_3H$; —$SO_2H$; —$PO_3H_2$; —$NO_2$; —$ONO_2$, —CNO, —SH, —CNS, —$OSO_3H$, —OC(O)(OH); halomethyl, dihalomethyl or trihalomethyl group or a fluorine, chlorine, bromine or iodine atom. Y is N, O, S, C—L or N—L, where L is H, alkyl, preferably $C_1$–$C_6$-alkyl, or an electronegative atom or functional group, such as, but not limited to, alkylcarbonyl; alkylthiocarbonyl; alkoxycarbonyl; aminocarbonyl; —OH; —CN; —$CO_2H$; —$SO_3H$; —$SO_2H$; —$PO_3H_2$; —$NO_2$; —$ONO_2$, —CNO, —SH, —CNS, —$OSO_3H$, —OC(O)(OH); halomethyl, dihalomethyl or trihalomethyl groups or a halogen atom, such as a fluorine, chlorine, bromine or iodine atom. Z and $Z_1$ are each, independently, O, S, CH, C═O, N, NH, N-alkyl, N-cycloalkyl and N—P, where P is a carbohydrate moiety, such as a monosaccharide group, for example, a fucosyl, glucosyl, galactosyl, mannosyl, fructosyl, gulosyl, idosyl, talosyl, allosyl, altrosyl, ribosyl, arabinosyl, xylosyl or lyxosyl group. $T_1$, $T_2$ and $T_3$ are each, independently, an $sp^2$- or $sp^3$-hybridized carbon or nitrogen atom. When f is 0, $T_3$ can further have the meanings given for Z and $Z_1$, above. a, b, c, d, e, f and i are each 0 or 1, provided that at least one of b and c is 1; at least one of d and e is 1 and at least one of f and i is 1.

$R_1$ is a monocyclic or polycyclic aryl or heteroaryl, oligo- or monosaccharide, alkyl, cycloalkyl, arylalkyl alkylamino or alkoxy group which is substituted with at least one substituent selected from the group consisting of electronegative atoms and electronegative functional groups. Preferred monosaccharide groups include fucosyl, glucosyl, galactosyl, mannosyl, fructosyl, gulosyl, idosyl, talosyl, allosyl, altrosyl, ribosyl, arabinosyl, xylosyl and lyxosyl groups. The electronegative substituent can be bonded to the aryl or heteroaryl ring system, or monosaccharide group either directly or indirectly via a bridging group, for example, an alkylene group such as a $C_1$–$C_4$-alkylene group or an oxaalkylene group. Suitable directly bonded and alkylene bridged electronegative atoms and functional groups include, but are not limited to, alkylcarbonyl; alkylthiocarbonyl; alkoxycarbonyl; aminocarbonyl; —OH; —CN; —$CO_2H$; —$SO_3H$; —$SO_2H$; —$PO_3H_2$; —$NO_2$; —$ONO_2$, —CNO, —SH, —CNS, —$OSO_3H$; —OC(O)(OH); carboxyalkyl, nitroalkyl, N,N-dialkylaminosulfonyl, aminocarbonyl, alkoxycarbonyl, alkoxycarbonylalkyl, cyanocarbonylalkyl, haloalkyl, such as fluoromethyl, difluoromethyl, trifluoromethyl, chloromethyl, dichloromethyl or trichloromethyl; alkyamido or a halogen atom, such as a fluorine, chlorine, bromine or iodine atom. In one embodiment, $R_1$ is selected from the group consisting of groups including, but not limited to, —$(CH_2)_a$COOH; —$(CH_2)_aNO_2$; —$(CH_2)_a$OH; —$(CH_2)_aPO_3H_2$; —$(CH_2)_a SO_3H$; —$(CH_2)_aSO_2H$; —$R_4(CH_2)_a$COOH; —$R_4(CH_2)_a NO_2$; —$R_4(CH_2)_aPO_3H_2$; —$R_4(CH_2)_aSO_2H$; —$R_4(CH_2)_a SO_3H$; and —$R_4(CH_2)_a$OH, where a is 1 to 12, preferably 1 to about 4, and $R_4$ is NH or 0.

Rings 1, 2 and 3 are each, independently, a five-or six-membered ring and, preferably, are each planar.

In another embodiment, the compound is of Formula 5, (5)

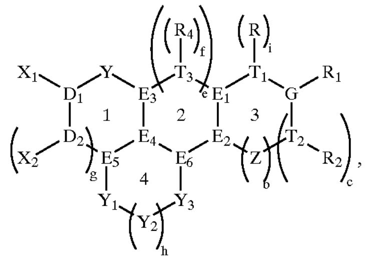

wherein $D_1$, $D_2$, $X_1$, $X_2$, $E_1$, $E_2$, $E_3$, $T_1$, $T_2$, $T_3$, Z, G, R, $R_1$, $R_2$, $R_4$, b, c e, f and i have the meanings given for these variables in Formula 2. $Y_1$, $Y_2$, and $Y_3$ are independently selected from the identities given for Y in Formula 2, and g and h are each, independently, 0 or 1. $E_5$ and $E_6$ are each, independently, an $sp^2$-hybridized carbon or nitrogen atom, and g is 0 or 1. Ring 4 can be further unsubstituted or substituted with one or more substituents, such as alkyl or aryl groups.

In one embodiment of the compounds of Formulas 1, 2, 3 and 5, $R_1$ is selected from the group consisting of substituted phenylene, naphthylene, quinolylene and other substituted aromatic and heteroaromatic groups. $R_1$ can also be a substituted ethynyl or poly(ethynyl) group. Suitable identities for $R_1$ include, but are not limited to, the groups shown below.

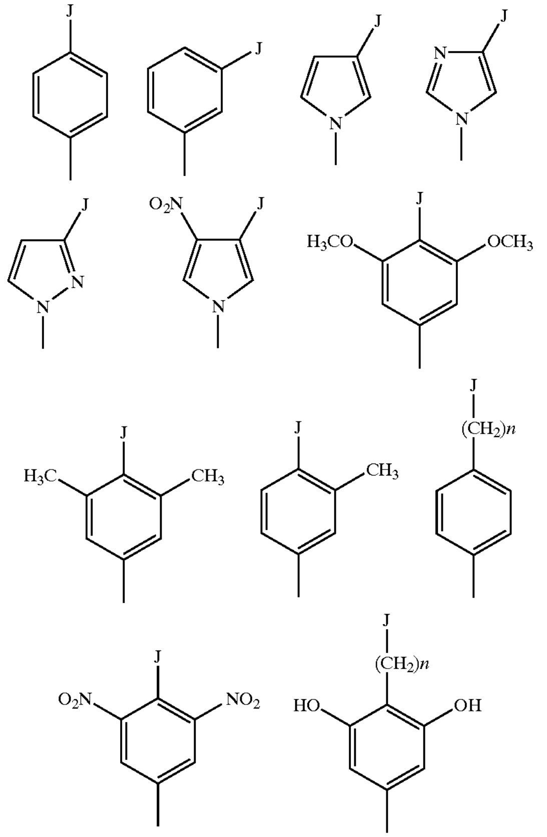

-continued

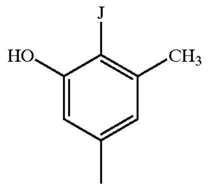
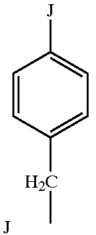
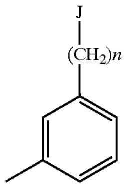
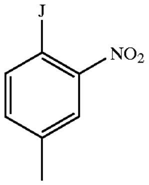
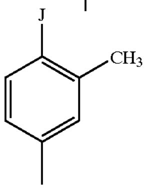
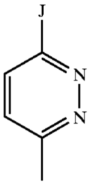
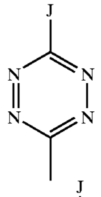
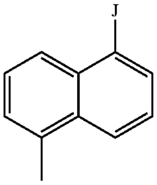
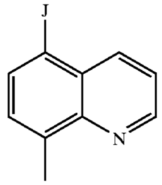
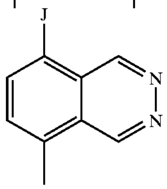
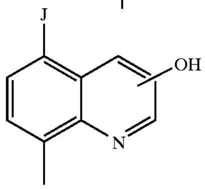
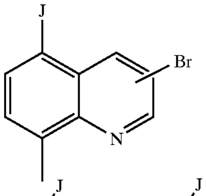
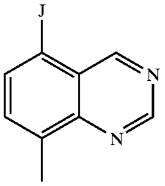
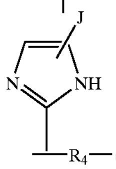
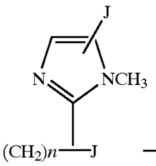

$-(CH_2)n-J$ $-R_4-(CH_2)n-J$ $-(C\equiv C)_n-J$

In each of these groups, J can be any of the electronegative atoms or groups described in the definition of $R_1$ in Formulas 1 and 2. Preferably, J is selected from the group consisting of —OH, —CN, $-NO_2$, $-CO_2H$, $-SO_3H$, $-SO_2H$, —F, —Cl, —Br, —I, $-PO_3H_2$, $-CF_3$, $-SO_2N(CH_3)_2$, $-C(O)NH_2$, $-C(O)CH_3$, $-C(O)OCH_3$, —C(O)CN, $-CH_2F$, $-CH_2Cl$, $-CF_2H$, $-CCl_2H$, $-CCl_3$ and $-NHC(O)CH_3$; $R_4$ is NH or O, and n is an integer from 0 to about 6.

Preferred compounds of Formula 1 are represented by Formulas 6–14, 16–18, 21–30 and 32–34, below. Preferred compounds of Formula 3 are represented by Formulas 15, 19, 20 and 31 below.

6

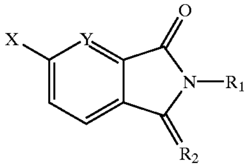

-continued

7

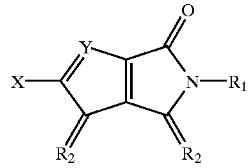

8

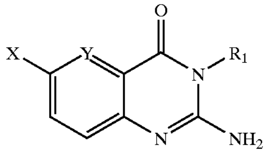

9

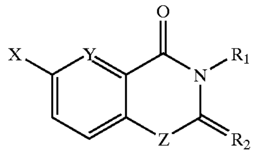

10

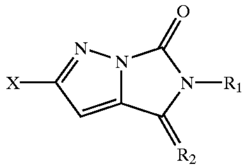

11

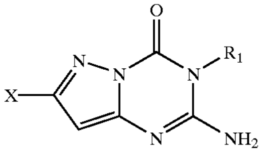

12

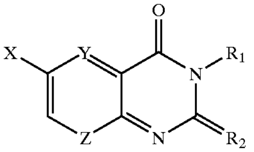

13

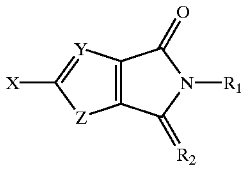

14

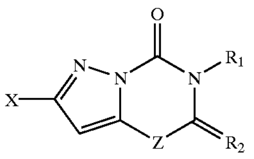

15

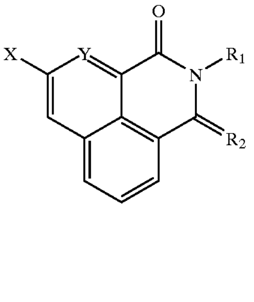

-continued
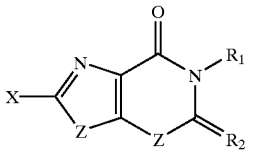
16
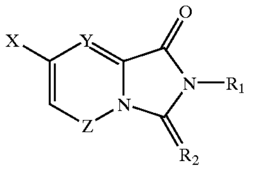
17
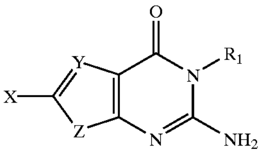
18
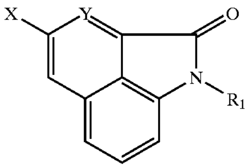
19
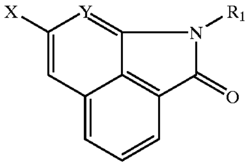
20
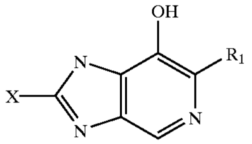
21
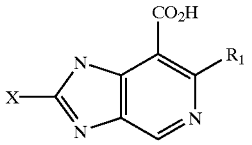
22
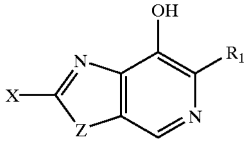
23
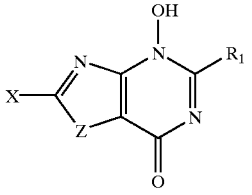
24
-continued
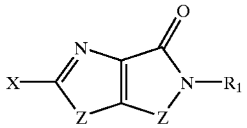
25
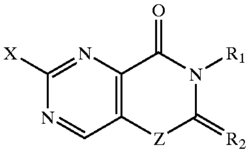
26
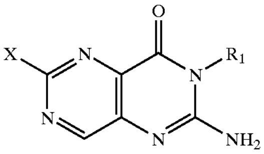
27
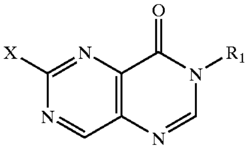
28
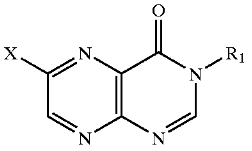
29
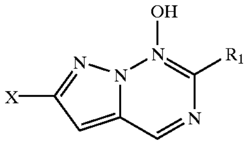
30
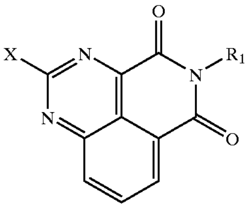
31
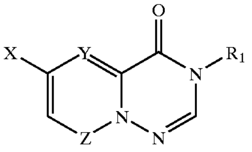
32
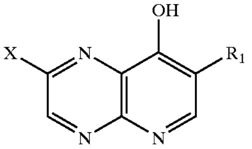
33
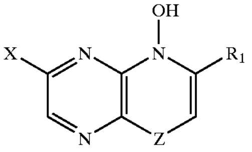
34
In each of Formulas 6–34, $R_1$, X and Y have the meanings given above for these variables in Formula 1. In Formulas 6, and 9–15, Z is selected from the group consisting of O, S, NH, N-alkyl, N-cycloalkyl and N-P, wherein P is a carbohydrate moiety, preferably a monosaccharide moiety, such as a fucosyl, glucosyl, galactosyl, mannosyl, fructosyl, gulosyl, idosyl, talosyl, allosyl, altrosyl, ribosyl, arabinosyl, xylosyl or lyxosyl group. In Formulas 6, 7, 9, 10 and 12–17, $R_2$ is selected from the group consisting of O, S, $CH_2$ and $NR_3$, wherein $R_3$ is H, OH, aryl or alkyl.

Preferred compounds of Formulas 2 and 5 are of Formulas 35–49 below.

35

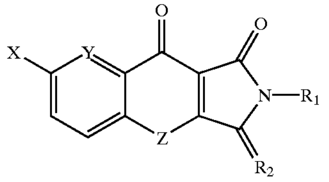

36

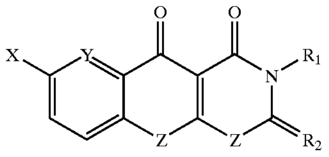

37

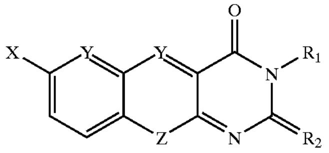

38

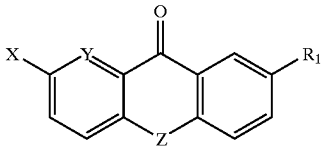

39

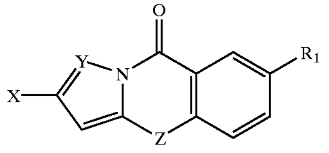

40

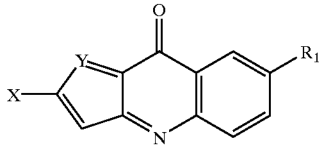

41

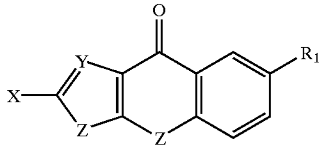

42

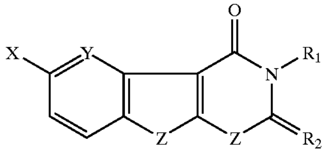

-continued

43

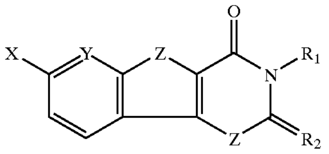

44

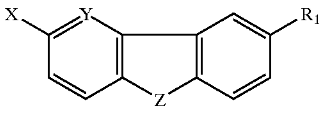

45

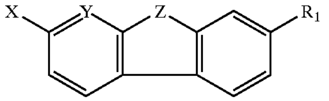

46

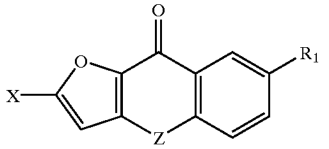

47

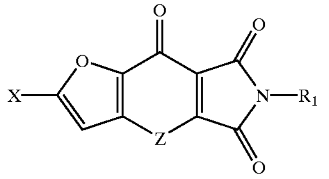

48

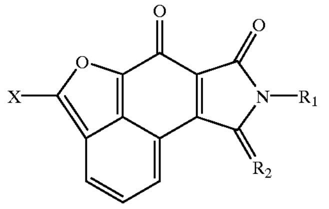

49

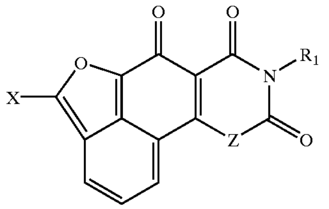

In Formulas 32–46, the structural variables X, $R_1$, $R_2$, Z and Y each have the identities given previously for Formula 2.

In another embodiment, the NGF/p75$^{NTR}$ binding inhibitor is of general formula 50, (50)

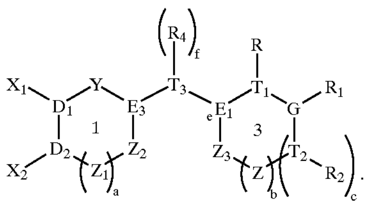

In Formula 50, the structural variables $D_1$, $D_2$, $X_1$, $X_2$, $E_1$, $E_2$, $E_3$, $T_1$, $T_2$, $T_3$, Z, G, R, $R_1$, $R_2$, $R_4$, b, and c have the meanings given for these variables in Formula 2. $T_3$ is an $sp^2$- or $sp^3$-hybridized carbon or nitrogen atom, and is preferably an $sp^2$-hybridized carbon or nitrogen atom.

A preferred subset of compounds of Formula 3 is represented by Formula 51, (51)

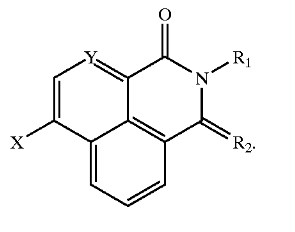

In Formula 51, X, Y and $R_1$ each have the meanings given for these variables in Formula 1. $R_2$ is O, S, $CH_2$ or N—$R_3$, wherein $R_3$ is H, OH, alkyl, preferably normal or branched $C_1$–$C_6$-alkyl, or aryl, such as phenyl or substituted phenyl.

In a preferred embodiment, the NGF/p75$^{NTR}$ inhibitor exhibits greater NGF/p75$^{NTR}$ binding inhibition in cells which express p75$^{NTR}$ but not trkA than in cells which express both p75$^{NTR}$ and trkA. The binding of NGF to p75$^{NTR}$ in cells which do not express trkA can, under certain conditions, mediate apoptotic cell death. The p75$^{NTR}$ receptor has a greater affinity for NGF in this proapoptotic state, that is, in cells which do not express trkA. Compounds which exhibit greater NGF/p75$^{NTR}$ binding inhibition in the absence of trkA advantageously selectively inhibit or interfere with processes such as apoptotic cell death, while having a smaller effect on other p75$^{NTR}$ mediated processes.

Preferred compounds which selectively inhibit the binding of NGF to p75$^{NTR}$ in cells which do not express trkA include compounds of Formulas 52 and 53, below.

52

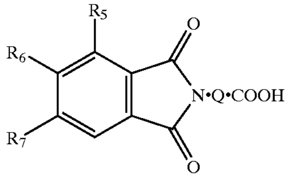

53

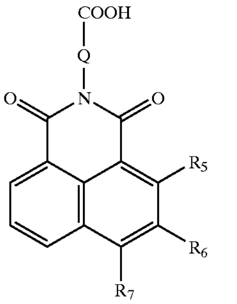

In Formulas 52 and 53, Q is selected from the group consisting of $C_1$–$C_5$-alkylene; para-and meta-phenylene; cycloalkylene, carbohydrate and para- and meta- —$CH_2C_6H_4$—. In Formulas 51 and 52, $R_5$, $R_6$ and $R_7$ are, preferably, each, independently, H, —COOH or —$NO_2$. More preferably, two of $R_5$, $R_6$ and $R_7$ are H and the other is —COOH or —$NO_2$.

The present invention also relates to a method of inhibiting the binding of NGF to p75$^{NTR}$. The method comprises contacting NGF in the presence of p75$^{NTR}$ with an NGF/p75$^{NTR}$ binding inhibitory amount of a NGF/p75$^{NTR}$ inhibitor compound, thereby inhibiting binding of NGF to p75$^{NTR}$. The method can be practiced in vitro, for example, in a cell culture screning assay to screen compounds which potentailly bind, activate or inhibit receptor function. In such a method, the inhibitor compound can function by binding and eliminating any competing function of NGF in the sample or culture. The inhibitor compounds can also be used to control NGF activity in neuronal cell culture. The method can also be practised in vivo, for example, to inhibit one or more processes mediated by binding of NGF to p75$^{NTR}$.

In another embodiment, the invention provides a method of treating a condition mediated by NGF/p75$^{NTR}$ binding in a patient. The method comprises the step of administering to the patient a therapeutically effective amount of a NGF/p75$^{NTR}$ binding inhibitor, such as any of the inhibitors described above. The condition to be treated can be any condition which is mediated, at least in part, by binding of NGF to the p75$^{NTR}$ receptor. Such conditions include, but are not limited to, Alzheimer's disease, epilepsy, pain, multiple sclerosis, amyotrophic lateral sclerosis, stroke and cerebral ischemia.

Preferably, the NGF/p75$^{NTR}$ binding inhibitor to be administered selectively inhibits the binding of NGF to p75$^{NTR}$ in cells which do not express trkA. In this embodiment, the condition is mediated, at least in part, by the binding of NGF to the p75$^{NTR}$ receptor in cells which do not express the trkA receptor. Generally, such conditions are mediated by NGF-induced apoptotic cell death.

The quantity of a given compound to be administered will be determined on an individual basis and will be determined, at least in part, by consideration of the individual's size, the severity of symptoms to be treated and the result sought. The NGF/p75$^{NTR}$ binding inhibitor can be administered alone or in a pharmaceutical composition comprising the inhibitor, an acceptable carrier or diluent and, optionally, one or more additional drugs.

The NGF/p75$^{NTR}$ binding inhibitor can be administered subcutaneously, intravenously, parenterally, intraperitoneally, intradermally, intramuscularly, topically, enteral (e.g., orally), rectally, nasally, buccally, sublingually, vaginally, by inhalation spray, by drug pump or via an implanted reservoir in dosage formulations containing conventional non-toxic, physiologically acceptable carriers or vehicles. The preferred method of administration is by oral delivery. The form in which it is administered (e.g., syrup, elixir, capsule, tablet, solution, foams, emulsion, gel, sol) will depend in part on the route by which it is administered. For example, for mucosal (e.g., oral mucosa, rectal, intestinal mucosa, bronchial mucosa) administration, nose drops, aerosols, inhalants, nebulizers, eye drops or suppositories can be used. The compounds and agents of this invention can be administered together with other biologically active agents, such as analgesics, anti-inflammatory agents, anesthetics and other agents which can control one or more symptoms or causes of a p75$^{NTR}$ mediated condition.

In a specific embodiment, it may be desirable to administer the agents of the invention locally to a localized area in need of treatment; this may be achieved by, for example, and not by way of limitation, local infusion during surgery, topical application, transdermal patches, by injection, by means of a catheter, by means of a suppository, or by means of an implant, said implant being of a porous, non-porous, or gelatinous material, including membranes, such as sialastic membranes or fibers. For example, the agent can be injected into the joints.

The compound of the invention can, optionally, be administered in combination with one or more additional drugs which, for example, are known for treating and/or alleviating symptoms of the condition mediated by $p75^{NTR}$ The additional drug can be administered simultaneously with the compound of the invention, or sequentially.

The present invention also provides pharmaceutical compositions. Such compositions comprise a therapeutically (or prophylactically) effective amount of one or more NGF/$p75^{NTR}$ binding inhibitors, preferably one or more compounds of Formulas 1, 2, 4 or 5, as described above, and a pharmaceutically acceptable carrier or excipient. Suitable pharmaceutically acceptable carriers include, but are not limited to, saline, buffered saline, dextrose, water, glycerol, ethanol, and combinations thereof. The carrier and composition can be sterile. The formulation should suit the mode of administration.

Suitable pharmaceutically acceptable carriers include but are not limited to water, salt solutions (e.g., NaCl), alcohols, gum arabic, vegetable oils, benzyl alcohols, polyethylene glycols, gelatin, carbohydrates such as lactose, amylose or starch, cyclodextrin, magnesium stearate, talc, silicic acid, viscous paraffin, perfume oil, fatty acid esters, hydroxymethylcellulose, polyvinyl pyrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition can be formulated in accordance with the routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

The pharmaceutical compositions of the invention can also include an agent which controls release of the NGF/$p75^{NTR}$ inhibitor compound, thereby providing a timed or sustained relase composition.

The present invention also relates to prodrugs of the NGF/$p75^{NTR}$ binding inhibitors disclosed herein, as well as pharmaceutical compositions comprising such prodrugs. For example, compounds of the invention which include acid functional groups or hydroxyl groups can also be prepared and administered as a corresponding ester with a suitable alcohol or acid. The ester can then be cleaved by endogenous enzymes within the patient to produce the active agent.

In a further embodiment, the invention relates to the use of an NGF/$p75^{NTR}$ binding inhibitor, such as any of the compounds described above, for treating a condition mediated by binding of NGF to $p75^{NTR}$. The invention further relates to the use of these compounds for the manufacture of a medicament for treating a condition mediated by binding of NGF to $p75^{NTR}$.

Figure 3:
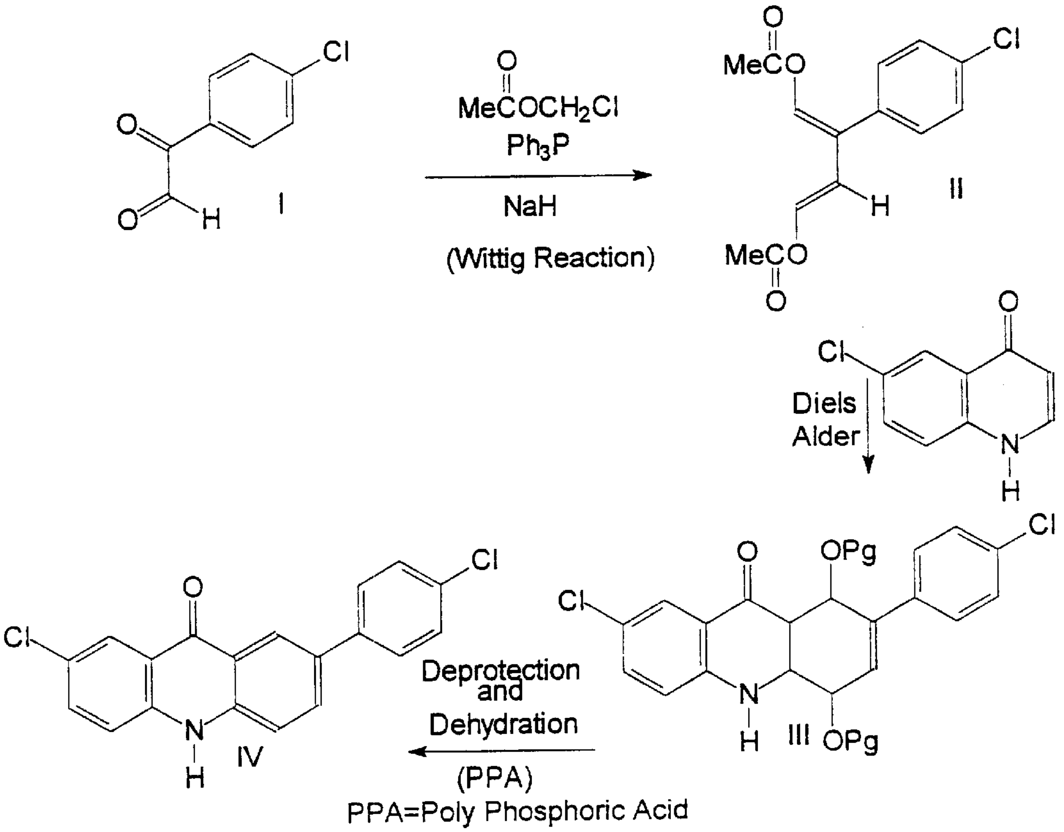
FIG. 3 sets forth a synthetic pathway for certain compounds of the invention; Pg=protecting group.
Figure 4:
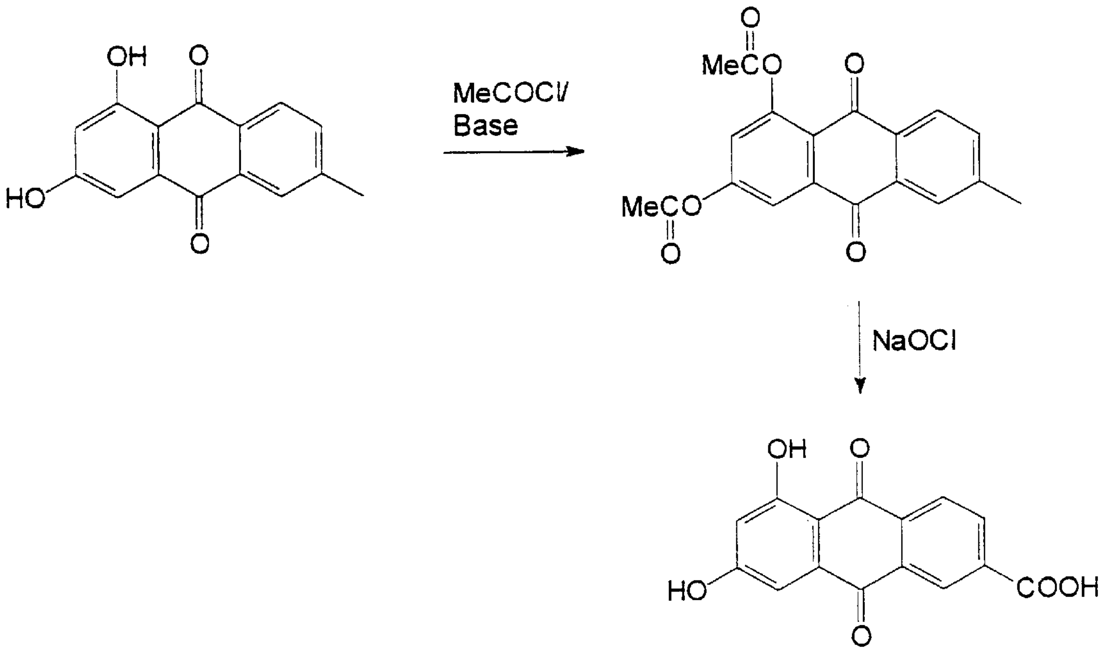
FIG. 4 sets forth a synthetic pathway for certain compounds of the invention.
Figure 5:
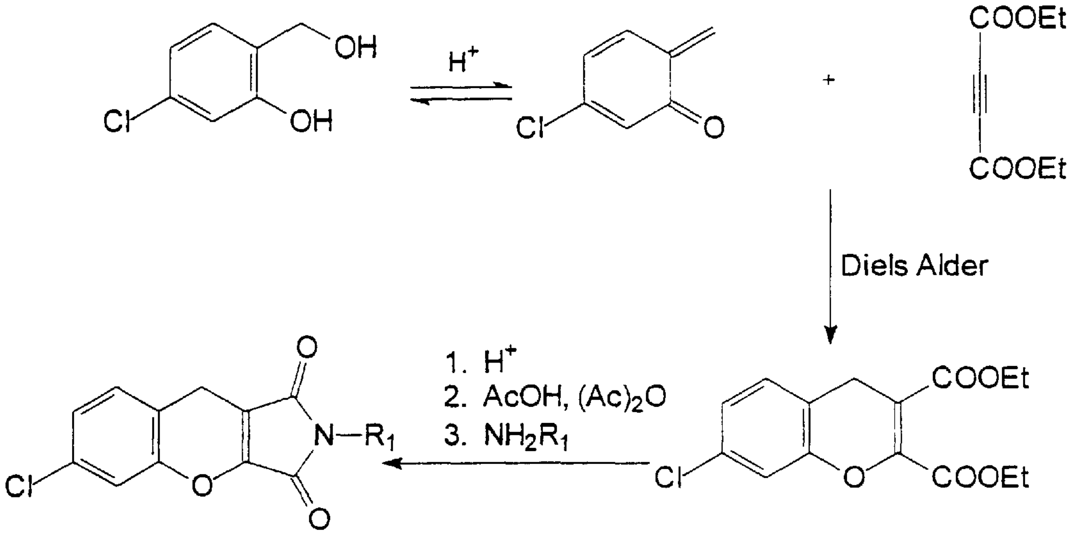
FIG. 5 sets forth a synthetic pathway for certain compounds of the invention.

Representative syntheses of compounds of the invention are set forth in the following examples. Other synthetic pathways that can be used to prepare certain compounds of the invention are illustrated in FIGS. 3 and 4.

EXAMPLES

Example 1

Synthesis of NGF/$p75^{NTR}$ inhibitors

General Methods

Reagents and solvents were obtained from commercial sources (Sigma, Aldrich, BDH). THF was dried by refluxing with benzophenone and potassium and subsequently distilled. All other solvents were utilized as they were received.

Thin layer chromatography (TLC) solvent systems used are given in Table 1. These were developed by ascending TLC on precoated aluminum backed sheets of silica gel 60 F254 (Merck). TLC plates were developed using ultra-violet light, iodine crystal and/or ninhydrin.

Melting points (mp) were determined on a Thomas Hoover Unimelt melting point apparatus and are uncorrected.

NMR of final compounds were determined on an AVANCE 300 MHz NMR spectrometer. All NMR samples were prepared in DMSO-d6 unless otherwise indicated. Chemical shifts are reported as δ parts per million using DMSO as an internal reference. Mass spectrometric (MS) analyses were obtained on a Varian Instrument VG Quattro multiple quadripole spectrometer using electrospray ionization (ESI). The spectra were all obtained in the negative ion mode. IR spectra were recorded on a Bomen MB-120 FT-IR spectrophotometer.

Abbreviations used herein are: HOAc, glacial acetic acid; THF, tetrahydrofuran; DMSO-$d_6$, deuterated dimethylsulfoxide; $CHCl_3$, chloroform: MeCN, acetonitrile; $H_2O$, distilled water; MeOH, methanol; EtOH, ethanol; TEA, triethylamine; EtOAc, ethyl acetate.

TABLE 1

List of Solvent Systems.

| Solvent Code | Solvent System | Solvent Ratio |
|---|---|---|
| A | MeOH:HOAc | 5:1 |
| B | MeCN:$H_2O$:MeOH | 8:1:1 |
| C | MeCN:$H_2O$:MeOH | 4:1:1 |
| D | $CHCl_3$:MeOH:HOAc | 95:10:3 |
| E | EtOH:HOAc | 50:1 |

General Synthesis of Naphthalimide Derivatives

Method A: The naphthalimide series of compounds was prepared through the condensation of stoichiometric amounts of 1,8-naphthalic anhydride or its derivative (I) with an appropriate primary amine (II). The combined reagents were dissolved in glacial acetic acid, dry THF, dry 1,4-dioxane or DMSO and placed under a $N_2$ atmosphere and refluxed. The progress of the reaction was monitored by TLC. Final clear solutions were concentrated in vacuo and the resulting crude material was either reprecipitated from 1,4-dioxane/1N HCl or HOAc/$H_2O$ and/or recrystallized from 95% ethanol, THF or 1,4-dioxane. In the instances where the final product precipitated out of the reaction solution, the completed reaction mixture was cooled to room temperature, the solid collected by filtration and washed with distilled water. This precipitate was reprecipitated with 1,4-dioxane/1N HCl or $HOAc/H_2O$ and/or recrystallized from 95% ethanol, THF or 1,4-dioxane. Purification also included fractional recrystallisation.

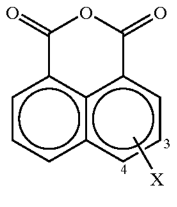

I $H_2N—R_1$ II where X and $R_1$ are as previously defined.

Method B: Reaction conditions and purification procedures were similar to those of method A. However, instead of stoichiometric amounts of reagents, the anhydride (I) and the primary amine(II) were combined in a 1:2 ratio with the optional addition of 1 equivalent of anhydrous sodium acetate. During the course of preparing the various naphthalimide derivatives, these reaction conditions were found to lead to increased product yields. Glacial acetic acid was the solvent of choice used under these conditions.

TABLE 2

Synthesized Naphthalimide Derivatives

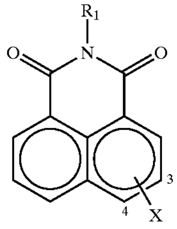

| Compd. | X | $R_1$ | Name |
|---|---|---|---|
| 200 | 3-$NO_2$ | $CH_2COOH$ | N-(1-carboxymethyl)-3-nitro-1,8-naphthalimide; 2-(1-carboxymethyl)-5-nitrobenzo[d,e]isoquinoline-1,3-dione |
| 201 | 3-$NO_2$ | $CH_2CH_2COOH$ | N-(2-carboxyethyl)-3-nitro-1,8-naphthalimide; 2-(2-carboxyethyl)-5-nitrobenzo[d,e]isoquinoline-1,3-dione |
| 202 | 3-$NO_2$ | $CH_2(CH_2)_2COOH$ | N-(3-carboxypropyl)-3-nitro-1,8-naphthalimide; 2-(3-carboxypropyl)-5-nitrobenzo[d,e]isoquinoline-1,3-dione |
| 203 | 3-$NO_2$ | $CH_2(CH_2)_3COOH$ | N-(4-carboxybutyl)-3-nitro-1,8-naphthalimide; 2-(4-carboxybutyl)-5-nitrobenzo[d,e]isoquinoline-1,3-dione |
| 204 | 3-$NO_2$ | $CH_2(CH_2)_4COOH$ | N-(5-carboxypentyl)-3-nitro-1,8-naphthalimide; 2-(5-carboxypentyl)-5-nitrobenzo[d,e]isoquinoline-1,3-dione |
| 220 | 4-$NO_2$ | $CH_2COOH$ | N-(1-carboxymethyl)-4-nitro-1,8-naphthalimide; 2-(1-carboxymethyl)-6-nitrobenzo[d,e]isoquinoline-1,3-dione |

TABLE 2-continued

Synthesized Naphthalimide Derivatives

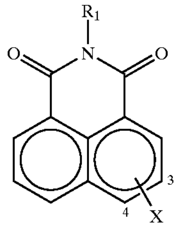

| Compd. | X | $R_1$ | Name |
|---|---|---|---|
| 221 | 4-$NO_2$ | $CH_2CH_2COOH$ | N-(2-carboxyethyl)-4-nitro-1,8-naphthalimide; 2-(2-carboxyethyl)-6-nitrobenzo[d,e]isoquinoline-1,3-dione |
| 222 | 4-$NO_2$ | $CH_2(CH_2)_2COOH$ | N-(3-carboxypropyl)-4-nitro-1,8-naphthalimide; 2-(3-carboxypropyl)-6-nitrobenzo[d,e]isoquinoline-1,3-dione |
| 223 | 4-$NO_2$ | $CH_2(CH_2)_3COOH$ | N-(4-carboxybutyl)-4-nitro-1,8-naphthalimide; 2-(4-carboxybutyl)-6-nitrobenzo[d,e]isoquinoline-1,3-dione |
| 224 | 4-$NO_2$ | $CH_2(CH_2)_4COOH$ | N-(5-carboxypentyl)-4-nitro-1,8-naphthalimide; 2-(5-carboxypentyl)-6-nitrobenzo[d,e]isoquinoline-1,3-dione |

Naphthalimide Derivatives:

Method A:

N-(1-Carboxymethyl)-3-nitro-1,8-naphthalimide (200)

3-nitro-1,8-naphthalic anhydride (1.0 g, 0.0041 mol) and glycine (0.31 g, 0.0041 mol) and 50–60 mls of glacial acetic acid were added to a 100 ml round-bottom flask equipped with a reflux condenser, heating mantle and stir plate. The system was placed under a $N_2$ atmosphere and heated to a gentle reflux. The progress of the reaction was monitored by TLC. After four days, the clear dark amber solution was concentrated under vacuum and the crude brown material reprecipitated with 1,4-dioxane/1N HCl. The precipitate was filtered through a Buchner funnel and washed with water. Successive fractional recrystallizations in ethanol afforded 0.35 g (28%) of 200 as a beige powder: M. Pt. 260–262° C.; TLC $R_f$ 0.83 (A): $R_f$ 0.82 (B): $R_f$ 0.23 (D): $^1H$ NMR (DMSO-$d_6$); IR ($cm^{-1}$): 2750–3100 (OH), 3077 (C═CH), 2665 (C—H), 1732 (C═O), 1711 (bs, C═O), 1670 (C═O), 1597 (C═C), 1538 (N═O), 1509 (C═C), 1430 (C═C), 1372 (C—O), 1341 (N—O), 1244 (C—O), 787 (C═CH). MS m/z (rel intensity) 299 (97) 255 (100), 281(93), 172 (26).

N-(2-Carboxyethyl)-3-nitro-1,8-naphthalimide (201)

3-nitro-1,8-naphthalic anhydride (1.0 g, 0.0041 mol) and β-alanine (0.37, 0.0041 mol) were refluxed as per 200 for 48 hours. Precipitate that formed during the course of the reaction was filtered and washed with water. The filtrate was concentrated under vacuum and the crude brown material reprecipitated with 1,4-dioxane/1N HCl. The precipitate was filtered through a Buchner funnel and washed with water. Both solids were combined and triturated with hot ethanol and 1,4-dioxane. Any undissolved material was removed by filtration. The combined ethanol and 1,4-dioxane fractions were concentrated in vacuo. Crystallization from ethanol afforded 0.38 g (30%) of 201 as a beige powder: M. Pt. 246–248° C.; TLC $R_f$ 0.74 (A): $R_f$ 0.84 (B): $R_f$ 0.67 (D): $^1H$ NMR (DMSO-$d_6$); IR ($cm^{-1}$): 2800–3130 (OH), 3071 (C═CH), 2646 (C—H), 1707 (bs, C═O), 1663 (C═O), 1625 (C═C), 1597 (C═C), 1537 (N═O), 1439 (C═C), 1420 (C═C), 1369 (C—O), 1347 (N—O), 1243 (C—O), 789 (C═CH). MS m/z (rel intensity) 313 (100) 241 (42).

N—(3-Carboxypropyl)-3-nitro-1,8-naphthalimide (202)

3-nitro-1,8-naphthalic anhydride (1.0 g, 0.0041 mol) and 4-aminobutyric acid (0.42 g, 0.0041 mol) were refluxed as per 200 for 48 hours. Resultant solution was purified as per 201 to afford 0.55 g (42%) of 202 as a fluffy beige solid: M. Pt. 200–202° C.; TLC $R_f$ 0.88 (A): $R_f$ 0.85 (B): $R_f$ 0.75 (D): $^1$H NMR(DMSO-$d_6$); IR(cm$^{-1}$): 2875–3100 (OH), 3062 (C═CH), 2560 (C—H), 1785 (C═O), 1702 (C═O), 1658 (C═O), 1625 (C═C), 1595 (C═C), 1538 (N═O), 1438 (C═C), 1418 (C═C), 1372 (C—O), 1334 (N—O), 1244 (C—O), 789 (C═CH). MS m/z (rel intensity) 327 (100) 241 (40).

N-(4-Carboxybutyl)-3-nitro-1,8-naphthalimide (203)

3-nitro-1,8-naphthalic anhydride (0.5 g, 0.0020 mol) and 5-aminopentanoic acid (0.24 g, 0.0020 mol) were refluxed in DMSO as per 200 for 24 hours. The dark orange brown solution was diluted with water until a beige precipitate formed. The precipitate was filtered through a Buchner funnel and washed copiously with water. The process was repeated on the concentrated filtrate. Combined solids were recrystallized in 1,4-dioxane/1N HCl. The filtered product was dried in air for a short time and then in vacuo for 48–72 hours to afford 0.43 g (63%) 203 as a beige feathery solid: M. Pt. 203–205° C.; TLC $R_f$ 0.92 (A): $R_f$ 0.89 (C): $R_f$ 0.26 (D): $^1$H NMR (DMSO-$d_6$); IR (cm$^{-1}$): 2700–3130 (OH), 3066 (C═CH), 1784 (C═O), 1706 (bs, C═O), 1659 (C═O), 1625 (C═C), 1596 (C═C), 1541 (N═O), 1458 (C═C), 1438 (C═C), 1351 (N—O), 1245 (C—O), 789 (C═CH). MS m/z (rel intensity) 341 (100), 241(16), 216 (24).

N-(5-Carboxypentyl)-3-nitro-1,8-naphthalimide (204)

3-nitro-1,8-naphthalic anhydride (1.0 g, 0.0041 mol) and 6-aminohexanoic acid (0.54 g, 0.0041 mol) were refluxed in 100 ml THF and 10 ml DMSO as per 200 for 24 hours. The dark brown solution was concentrated and manipulated as per 203 to yield 1.0 g (67%) 204 as beige powder: M. Pt. 192–194° C.; TLC $R_f$ 0.70 (A): $R_f$ 0.91 (B): $R_f$ 0.63 (D): $^1$H NMR (DMSO-$d_6$) δ 1.36 (m, 2H), 1.54 (m, 2H), 1.64 (m, 2H), 2.22 (t, J=7.3 Hz, 2H), 4.02 (t, J=7.3 Hz, 2H), 8.02 (dd, J=7.1, 8.3 Hz, 1H), 8.63 (d, J=7.1 Hz, 1H), 8.73 (d, J=8.3 Hz, 1 Hz), 8.89 (d, J=2.3 Hz, 1H), 9.43 (d, J=2.3 Hz, 1H); IR (cm$^{-1}$): 2700–3175 (OH), 3075 (C═CH), 2688 (C—H), 1706 (bs, C═O), 1663 (C═O), 1625 (C═C), 1598 (C═C), 1533 (N═O), 1437 (C═C), 1419 (C═C), 1348 (N—O), 1244 (C—O), 791 (C═CH). MS m/z (rel intensity) 355 (100).

N-(2-Carboxyethyl)-4-nitro-1,8-naphthalimide (221)

4-nitro-1,8-naphthalic anhydride (0.5 g, 0.0020 mol) and β-alanine (0.18 g, 0.0020 mol) were refluxed for 4 days and the final mixture purified as per 200. Successive fractional recrystallisations in $CHCl_3$ afforded 0.24 g (38%) 221 as an beige solid: M. Pt. 224–225° C.; TLC $R_f$ 0.77 (A): $R_f$ 0.80 (C): $R_f$ 0.46 (D): $^1$H NMR (DMSO-$d_6$); IR (cm$^{-1}$): 2800–3175 (OH), 3077 (C═CH ), 2637 (C—H), 1788 (C═O), 1705 (bs, C═O), 1657 (C═O), 1624 (C═C), 1594 (C═C), 1534 (N═O), 1440 (C═C), 1408 (C═C), 1346 (N—O), 1229 (C—O), 789 (C═CH). MS m/z (rel intensity) 314 (16), 313 (100), 274 (50).

N-(3-Carboxypropyl)-4-nitro-1,8-naphthalimide (222)

4-nitro-1,8-naphthalic anhydride (0.5 g, 0.0020 mol) and 4-aminobutyric acid (0.21 g, 0.0020 mol) were refluxed for 5 days in dry THF as per 200. The dark orange amber solution was concentrated to 20 ml in vacuo and diluted with 1N HCl until a beige precipitate formed. The precipitate was filtered through a Buchner funnel and washed with water. The crude material was reprecipitated from 1,4-dioxane/1N HCl and filtered. Successive fractional recrystallisations in $CHCl_3$ afforded 0.22 g (34%) of 222 as a beige solid: M. Pt. 179–180° C.; $R_f$ 0.85 (A): TLC $R_f$ 0.81 (B): $R_f$ 0.48 (D): $^1$H NMR (DMSO-$d_6$); IR (cm$^{-1}$): 2780–3200 (OH), 3075 (C═CH), 2688 (C—H), 1778 (C═O), 1705 (bs, C═O), 1655 (C═O), 1624 (C═C), 1584 (C═C), 1534 (N═O), 1439 (C═C), 1409 (C═C), 1344 (N—O), 1231 (C—O), 789 (C═CH). MS m/z (rel intensity) 328 (20), 327 (100), 274 (27), 241 (36).

N-(4-Carboxybutyl)-4-nitro-1,8-naphthalimide (223)

4-nitro-1,8-naphthalic anhydride (0.5 g, 0.0020 mol) and 5-aminopentanoic acid (0.24 g, 0.0020 mol) were refluxed for 3 days in dry THF as per 200. The dark orange amber solution was purified as per 222 to afford 0.27 g (40%) of 223 as a orange powder: M. Pt. 198–200° C.; TLC $R_f$ 0.84 (A): $R_f$ 0.88 (C): $R_f$ 0.46 (D): $^1$H NMR (DMSO-$d_6$); IR (cm$^{-1}$): 2825–3130 (OH), 3077 (C═CH), 2670 (C—H), 1704 (bs, C═O), 1660 (C═O), 1624 (C═C), 1583 (C═C), 1529 (N═O), 1435 (C═C), 1411 (C═C), 1345 (N—O), 1233 (C—O), 787 (C═CH). MS m/z (rel intensity) 342 (19), 341 (100), 274 (20), 241 (40).

N-(5-Carboxypentyl)-4-nitro-1,8-naphthalimide (224)

4-nitro-1,8-naphthalic anhydride (0.5 g, 0.0020 mol) and 6-aminohexanoic acid (0.27 g, 0.0020 mol) were refluxed for 3 days in dry THF and the final mixture purified as per 223. Crystallization from THF/1N HCl afforded 0.65 g (95%) of 224 as a beige solid: M. Pt. 168–169° C.; TLC $R_f$ 0.85 (A): $R_f$ 0.81 (B): $R_f$ 0.50 (D): $^1$H NMR (DMSO-$d_6$); IR (cm$^{-1}$): 2775–3175 (OH), 3078 (C═CH), 2670 (C—H), 1716 (bs, C═O), 1661 (C═O), 1624 (C═C), 1594 (C═C), 1521 (N═O), 1436 (C═C), 1409 (C═C), 1339 (N—O), 1261 (C—O), 785 (C═CH). MS m/z (rel intensity) 365 (21), 355 (100).

Method B:

N-(1-Carboxymethyl)-4-nitro-1,8-naphthalimide (220)

4-nitro-1,8-naphthalic anhydride (1.0 g, 0.0041 mol), glycine (0.38 g, 0.0082 mol), anhydrous sodium acetate (0.51 g, 0.61 mol) and 70–80 mfs of glacial acetic acid were added to a 100 ml round-bottom flask equipped with a reflux condenser, heating mantle and stir plate. The system was placed under a $N_2$ atmosphere and heated to a gentle reflux. After 3 days, the dark amber solution was concentrated to 15–20 ml under vacuum with a rotary evaporator. Ensuing precipitate was filtered and washed twice with 5 ml 1N HCl and twice with 5 ml water. Crystallization from 1,4-dioxane/$H_2O$ afforded 0.6 g (50%) 220 as a beige solid: M. Pt. 263–264° C.; TLC $R_f$ 0.81 (A): $R_f$ 0.84 (C): $R_f$ 0.35 (D): $^1$H NMR (DMSO-$d_6$) δ 4.74 (s, 2H), 8.10 (dd, J=8.4, 8.0 Hz, 1H), 8.55 (d, J=7.6 Hz, 1H), 8.63 (d, J=8.0 Hz, 1H), 8.65 (d, J=8.0, 1H), 8.73 (d, J=8.4 Hz, 1H); IR (cm$^{-1}$) 2850–3150 (OH), 3077 (C═CH), 2671 (C—H), 1711 (C═O), 1674 (bs, C═O), 1625 (C═C), 1583 (C═C), 1531 (N═O), 1429 (C═C), 1334 (N—O), 1232 (C—O), 785 (C═CH). MS m/z (rel intensity) 299 (100), 255 (280).

Example 2

Assessment of NGF/p75$^{NTR}$ Binding Inhibition

The radio-iodination and receptor binding of NGF (Sutter et al., 1979) was performed with modifications (Ross et al., 1997) as follows: Evaluation of the ability of NCP compounds to inhibit TrkA and p75$^{NTR}$ binding was determined by the binding of $^{125}$I-NGF to PC12 cells (rat pheochromocytoma cells expressing TrkA and p75$^{NTR}$ obtained from ATCC) and PC12$^{nnr5}$ (rat pheocliromocytoma cells expressing p75$^{NTR}$ only; obtained from Dr. L. Greene, Columbia University, NY). The p75$^{NTR}$ is in a low affinity state and a high affinity state, respectively, in these cell types (Ross et al., 1998). PC12 and PC12$^{nnr5}$ cells were grown in RPMI (Sigma) with 10% heat inactivated donor horse serum and 5% fetal calf serum. Cells were harvested by replacing the medium with calcium, magnesium-free balanced salt solution (Gey's solution) and incubating at 37° C. for 15 minutes. Cells were pelleted by centrifugation and suspended in HKR buffer (10 mM Hepes [pH 7.35] containing 125 mM NaCl, 4.8 mM KCl, 1.3 mM $CaCl_2$, 1.2 mM $MgSO_4$, 1.2 mM $KH_2PO_4$, 1 g/L glucose and 1 g/L BSA) at a cell concentration of $2\times10^6$/mL and kept at 4° C. Triplicate tubes were set up for total binding, non-specific binding and binding in the presence of candidate competitor molecule (i.e., a tube for each data point). Each tube contained $^{125}$I-NGF (at 1 nM), 400,000 cells (for a final cell concentration of $10^6$/mL) and NGF (50 nM, to define non-specific binding), as required. The tubes were incubated for 2 h at 4° C. and specific binding evaluated by measuring specifically bound DPM (Ross et al., 1997). Data were analysed and the results expressed as receptor binding observed in the presence of competitor as a percentage of receptor binding in the absence of a competitor.

TABLE 3

Results of in vitro binding inhibition assays

| Compound (50 μM) | PC12 % of Max | nnr5 % of Max |
|---|---|---|
| 200 | 92, 87, 74 = 84 | 58, 63, 64 = 62 |
| 201 | 27, 32, 41 = 33 | 30, 4, 34 = 23 |
| 202 | 21, 22, 30 = 24 | 16, 0, 0 = 5 |
| 203 | 36, 41, 35 = 37 | 33, 0, 18 = 17 |
| 204 | 41, 41, 36 = 39 | 12, 0, 47 = 20 |
| 220 NS | 37, 43, 49 = 43 | 21, 17, 26 = 21 |
| 221 | 29, 32, 31 = 31 | 41, 37, 42 = 40 |
| 222 NS | NT | NT |
| 223 | 27, 33, 33 = 31 | 40, 41, 47 = 43 |
| 224 | 31, 34, 22 = 29 | 36, 35, 39 = 36 |

NS: Not Soluble @ 100 μM DMSO
NT: Not Tested

While this invention has been particularly shown and described with references to preferred embodiments thereof, it will be understood by those skilled in the art that various changes in form and details may be made therein without departing from the spirit and scope of the invention as defined by the appended claims.

REFERENCES CITED

Barbacid, *Oncogene* 8:2033–2042 (1993)
Barde, *Neuron* 2:1525–1534 (1989)
Barker and Shooter, *Neuron* 13:203–215 (1994)
Ben Ari and Represa, *TINS* 13:312–318 (1990)
Berkemeier et al., *Neuron* 7:857–866 (1991)
Bothwell, *Cell* 65:915–918 (1991)
Bothwell and Shooter, *J. Biol. Chem.* 23:8532–8536 (1977)
Bradshaw et al., *Protein Science* 3:1901–1913 (1994)
Burton et al., *J. Neurochem.* 59:1937–1945 (1992)
Burton et al., *Soc. Neurosci. Abs.* 21:1061 (1995)
Carter et al., *Science* 272:542–545 (1996)
Cassacia-Bonnefil et al., *Nature* 383:716–719 (1996)
Chao, *Neuron* 9:583–593 (1992b)
Chao, *J. Neurobiol.* 25:1373–1385 (1994)
Chao and Hempstead, *Trends Neurosci.* 18:321–326 (1995)
Dobrowsky et al., *Science* 265:1596–1599 (1994)
Drinkwater et al, *J. Biol Chem.* 268:23202–23207 (1993)
Escandon et al., *Neurosci. Res.* 34:601–613 (1993)
Gotz et al., *Nature* 372:266–269 (1994)
Gregory et al., *Protein Engineering* 6:29–35 (1993)
Hallböök et al., *Neuron* 6:845–858 (1991)
Hefti, *J. Neurosci.* 6:2155–2162 (1986)
Hefti and Weiner, *Annals of Neurology* 20:275–281 (1986)
Heldin et al., *J. Biol. Chem.* 264:8905–8912 (1989)
Hempstead et al., *Nature* 350:678–683 (1991)
Herrmann et al., *Mol. Biol.* 4:1205–1216 (1993)
Hohn et al., *Nature* 344:339–341 (190)
Ibáñez et al., *Cell* 69:329–341 (1992)
Ibáñez et al., *EMBO J.* 12:2281–2293 (1993)
Ibáñez, *Trends Biotech.* 13:217–227 (1995)
Jing et al., *Neuron* 9:1067–1079 (1992)
Kahle et al., *J. Biol. Chem.* 267:22707–22710 (1992)
Kaplan et al., *Science* 252:554–558 (1991)
Klein et al., *Cell* 65:189–197 (1991)
Klein et al., *Neuron* 8:947–956 (1992)
Lamballe et al., *Cell* 66:967–970 (1991)
Landreth and Shooter, *Proc. Natl. Acad. Sci. U.S.A.* 77:4751–4755 (1980)
Leibrock et al., *Nature* 341:149–152 (1989)
Leven and Mendel, *TINS* 16:353–359 (1993)
Levi-Montalcini, *EMBO J.* 6:1145–1154 (1987)
Luo and Neet, *J. Biol. Chem.* 267:12275–12283 (1992)
Mahadeo et al., *J. Biol. Chem.* 269:6884–6891 (1994)
Maisonpierre et al., *Science* 247:1446–1451 (1990)
Maness et al., *Neurosci. Biobehav. Rev.* 18:143–159 (1994)
Marchetti et al., *Cancer Res.* 56:2856–2863 (1996)
Matsumoto et al., *Cancer Res.* 55:1798–1806 (1995)
McDonald et al., *Nature* 354:411–414 (1991)
McKee et al., *Ann. Neurol.* 30:156 (1991)
McMahon et al., *Nature Med.* 1:774–780 (1995)
Meakin and Shooter, *Trends Neurosci.* 15:323–331 (1992)
Moore and Shooter, *Neurobiology* 5:369–381 (1975)
Radziejewski et al., *Biochemistry* 31:4431–4436 (1992)
Rashid et al., *Proc. Natl. Acad. Sci. U.S.A.* 92:9495–9499 (1995)
Rodrigues-Tébar et al., *Neuron* 4:487–492 (1990)
Rodrigues-Tébar et al., *EMBO J.* 11:917–922 (1992)
Rosenthal et al., *Neuron* 4:767–773 (1990)
Ross et al., *J. Cell Biol.* 132:945–953 (1996)
Ross et al., *Nature Med.* 3:872–878 (1997)
Ross et al. *Eur. J. Neurosci.* 10 890–898 (1998)
Rydén and Ibáñez, *J. Biol. Chem.* 271:5623–5627 (1996)
Schechter and Bothwell, *Cell* 24:867–874 (1981)
Shamovsky et al., *Can. J. Chem.* 76:1389–1401 (1998)
Sharnovsky et al., *J. Am Chem Soc* 118:9743–9749 (1999)
Shih et al., *J. Biol. Chem.* 269:27679–27686 (1994)
Soppet et al., *Cell* 65:895–903 (1991)
Squinto et al., *Cell* 65:885–893 (1991)
Suter et al., *J. Neurosci.* 12:306–318 (1992)
Sutter et al., *J. Biol. Chem.* 254:5972–5982 (1979)
Taylor et al., *Soc. Neurosci. Abs.* 17:712 (1991)
Treanor et al., *J. Biol. Chem.* 270:23104–23110 (1995)
Vale and Shooter, *Methods Enzymol.* 109:21–39 (1985)
Van der Zee et al., *Science* 274:1729–1732 (1996)
Washiyama et al., Amer. *J. Path.* 148:929–940 (1996)
Wolf et al., *J. Biol. Chem.* 270:2133–2138 (1995)
Woolf and Doubell, *Current Opinions in Neurobiol.* 4:525–534 (1994)

What is claimed is:

1. A method of inhibiting the binding of nerve growth factor to the p75$^{NTR}$ receptor, comprising contacting cells expressing the p75$^{NTR}$ receptor with an effective inhibiting amount of a compound having the chemical structure defined in the following formula

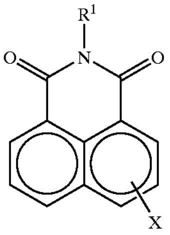

or a pharmaceutically acceptable salt thereof;

wherein:

$R^1$ is selected from —$CH_2COOH$ and —$CH_2(CH_2)_4COOH$; and

X is selected from the group consisting of

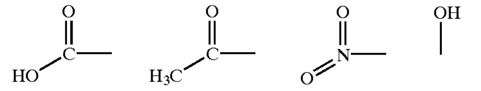

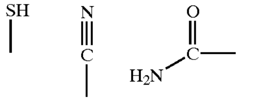

and

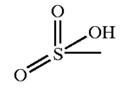

;

with the proviso that when X is —$NO_2$, $R^1$ is $CH_2(CH_2)_4COOH$.

2. A method of inhibiting the binding of nerve growth factor to the p75$^{NTR}$ receptor, comprising contacting cells expressing the p75$^{NTR}$ receptor with an effective inhibiting amount of N-(5-carboxypentyl)-3-nitro-1,8-naphthalimide or a pharmaceutically acceptable salt thereof.

3. A method of inhibiting the binding of nerve growth factor to the p75$^{NTR}$ receptor, comprising contacting cells expressing the p75$^{NTR}$ receptor with an effective inhibiting amount of N-(5-carboxypentyl)-4-nitro-1,8-naphthalimide or a pharmaceutically acceptable salt thereof.

4. A method of inhibiting the binding of nerve growth factor to the p75$^{NTR}$ receptor, comprising contacting cells expressing the p75$^{NTR}$ receptor with an effective inhibiting amount of a pharmaceutical composition comprising a compound having the chemical structure defined in the following formula

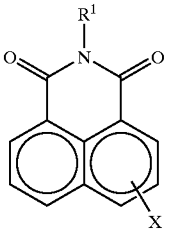

or a pharmaceutically acceptable salt thereof;

wherein:

$R^1$ is selected from —$CH_2COOH$ and —$CH_2(CH_2)_4COOH$; and

X is selected from the group consisting of

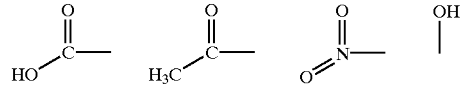

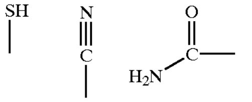

and

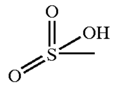

;

with the proviso that when X is —$NO_2$, $R^1$ is —$CH_2(CH_2)_4COOH$, together with a pharmaceutically acceptable carrier or excipient.

5. A method of inhibiting the binding of nerve growth factor to the p75$^{NTR}$ receptor, comprising contacting cells expressing the p75$^{NTR}$ receptor with an effective inhibiting amount of a pharmaceutical composition comprising N-(5-carboxypentyl)-3-nitro-1,8-naphthalimide or a pharmaceutically acceptable salt thereof, together with a pharmaceutically acceptable carrier or excipient.

6. A method of inhibiting the binding of nerve growth factor to the p75$^{NTR}$ receptor, comprising contacting cells expressing the p75$^{NTR}$ receptor with an effective inhibiting amount of a pharmaceutical composition comprising N-(5-carboxypentyl)-4-nitro-1,8-naphthalimide or a pharmaceutically acceptable salt thereof, together with a pharmaceutically acceptable carrier or excipient.

7. A method of treating a condition characterized by nerve growth factor-mediated cell apoptosis in a patient, the method comprising the step of administering to the patient a therapeutically effective amount of a compound having the chemical structure defined in the following formula

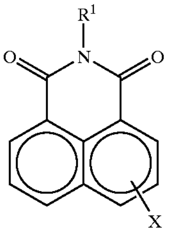

or a pharmaceutically acceptable salt thereof;

wherein:

$R^1$ is selected from —$CH_2COOH$ and —$CH_2(CH_2)_4COOH$; and

X is selected from the group consisting of

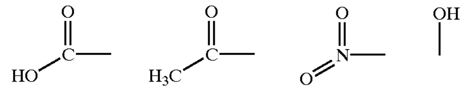

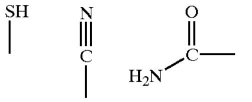

and

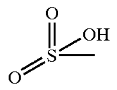

;

with the proviso that when X is —$NO_2$, $R^1$ is —$CH_2(CH_2)_4COOH$.

8. A method of treating a condition characterized by nerve growth factor-mediated cell apoptosis in a patient, the method comprising the step of administering to the patient a therapeutically effective amount of N-(5-carboxypentyl)-3-nitro-1,8-naphthalimide or a pharmaceutically acceptable salt thereof.

9. A method of treating a condition characterized by nerve growth factor-mediated cell apoptosis in a patient, the method comprising the step of administering to the patient a therapeutically effective amount of N-(5-carboxypentyl)-4-nitro-1,8-naphthalimide or a pharmaceutically acceptable salt thereof.

10. A method of treating a condition characterized by nerve growth factor-mediated cell apoptosis in a patient, the method comprising the step of administering to the patient a therapeutically effective amount of a pharmaceutical composition comprising a compound having the chemical structure defined in the following formula

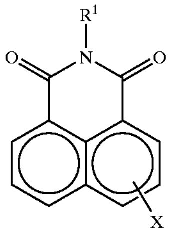

or a pharmaceutically acceptable salt thereof;

wherein:

$R^1$ is selected from $—CH_2COOH$ and $—CH_2(CH_2)_4COOH$; and

X is selected from the group consisting of

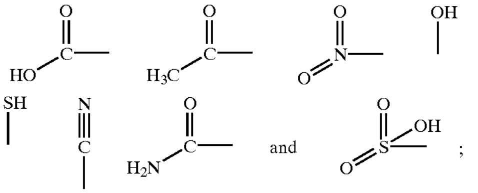

and ;

with the proviso that when X is $—NO_2$, $R^1$ is $—CH_2(CH_2)_4COOH$, together with a pharmaceutically acceptable carrier or excipient.

11. A method of treating a condition characterized by nerve growth factor-mediated cell apoptosis in a patient, the method comprising the step of administering to the patient a therapeutically effective amount of a pharmaceutical composition comprising N-(5-carboxypentyl)- 3-nitro-1,8-naphthalimide or a pharmaceutically acceptable salt thereof, together with a pharmaceutically acceptable carrier or excipient.

12. A method of treating a condition characterized by nerve growth factor-mediated cell apoptosis in a patient, the method comprising the step of administering to the patient a therapeutically effective amount of a pharmaceutical composition comprising N-(5-carboxypentyl)- 4-nitro-1,8-naphthalimide or a pharmaceutically acceptable salt thereof, together with a pharmaceutically acceptable carrier or excipient.

13. The method defined in claim 7, wherein the condition is selected from the group consisting of Alzheimer's disease, epilepsy, multiple sclerosis, amyotrophic lateral sclerosis, stroke and pain.

14. The method defined in claim 8, wherein the condition is selected form the group consisting of Alzheimer's disease, epilepsy, multiple sclerosis, amyotrophic lateral sclerosis, stroke and pain.

15. The method defined in claim 9, wherein the condition is selected from the group consisting of Alzheimer's disease, epilepsy, multiple sclerosis, amyotrophic lateral sclerosis, stroke and pain.

16. The method defined in claim 10, wherein the condition is selected from the group consisting of Alzheimer's disease, epilepsy, multiple sclerosis, amyotrophic lateral sclerosis, stroke and pain.

17. The method defined in claim 11, wherein the condition is selected from the group consisting of Alzheimer's disease, epilepsy, multiple sclerosis, amyotrophic lateral sclerosis, stroke and pain.

18. The method defined in claim 12, wherein the condition is selected from the group consisting of Alzheimer's disease, epilepsy, multiple sclerosis, amyotrophic lateral sclerosis, stroke and pain.

* * * * *

UNITED STATES PATENT AND TRADEMARK OFFICE

CERTIFICATE OF CORRECTION

PATENT NO. : 6,492,380 B1
DATED : December 10, 2002
INVENTOR(S) : Gregory M. Ross It is certified that error appears in the above-identified patent and that said Letters Patent is hereby corrected as shown below:

Column 2,
Line 31, "$LyS^{88}$" should be -- $Lys^{88}$ --;

Column 6,
Line 36, "coloration" should be -- conformation" --;

Column 21,
Line 59, "relase" should be -- release --;

Column 26,
Line 40, "mfs" should be -- mls --; and

Column 28,
Line 53, "Sharnovsky" should be -- Shamovsky --.

Signed and Sealed this

Ninth Day of December, 2003

JAMES E. ROGAN
*Director of the United States Patent and Trademark Office*